United States Patent [19]
Iijima et al.

[11] Patent Number: 4,628,057
[45] Date of Patent: Dec. 9, 1986

[54] TETRAHYDRO-β-CARBOLINE DERIVATIVES AND TREATMENT OF LIVER DISEASES

[75] Inventors: Ikuo Iijima, Urawa; Yutaka Saiga, Ageo; Toshikazu Miyagishima, Wako; Yuzo Matsuoka, Tondabayashi; Mamoru Matsumoto, Nara, all of Japan

[73] Assignee: Tanabe Seiyaku Co., Ltd., Osaka, Japan

[21] Appl. No.: 666,481

[22] Filed: Oct. 30, 1984

[30] Foreign Application Priority Data

Nov. 12, 1983 [GB] United Kingdom ............... 8330260

[51] Int. Cl.$^4$ .................. A61K 31/395; C07D 471/02
[52] U.S. Cl. ...................................... 514/292; 546/85; 546/86; 546/87; 546/63; 544/60
[58] Field of Search .................. 546/85, 86, 87, 63; 544/60; 514/292

[56] References Cited

U.S. PATENT DOCUMENTS

| | | | |
|---|---|---|---|
| 2,187,719 | 1/1940 | Williams | 548/523 |
| 4,336,260 | 6/1982 | Payne et al. | 546/85 |

FOREIGN PATENT DOCUMENTS

| | | | |
|---|---|---|---|
| 20923 | 2/1961 | Fed. Rep. of Germany | 546/85 |
| 1837 | 5/1963 | France | 546/85 |

OTHER PUBLICATIONS

Goodman and Gilman, The Pharmacological Basis of Therapeutics, 6th Ed. p. 28.

Primary Examiner—Henry R. Jiles
Assistant Examiner—J. Richter
Attorney, Agent, or Firm—Birch, Stewart, Kolasch & Birch

[57] ABSTRACT

Novel tetrahydro-β-carboline derivatives of the formula:

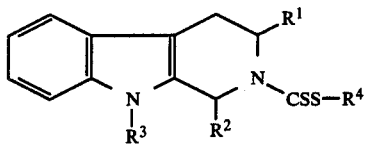

wherein
  $R^1$ is carboxyl, a lower alkoxycarbonyl, carbamoyl, an N,N-di-lower alkylcarbamoyl, an N-(phenyl-substituted lower alkylidenamino)carbamoyl, a [N,N-di(lower alkyl)amino]-lower alkyl, or a nitrogen-containing monocyclic heterocyclic group;
  $R^2$ is hydrogen atom, a lower alkyl, or a hydroxy-lower alkyl group, or $R^2$ is combined with $R^1$ to form a group: —CO—O—CH$_2$—;
  $R^3$ is hydrogen atom, a lower alkyl, a phenyl-lower alkyl, or a group: —CSS—$R^4$;
  $R^4$ is hydrogen atom, an alkyl, or a group: —(CH$_2$)$_n$Y$^1$;
  n is 0, 1 or 2,
  $Y^1$ is a lower alkenyl, a phenyl-substituted lower alkenyl, an N,N-di(lower alkyl)amino, a lower alkylmercapto, a lower alkoxycarbonyl, benzoyl, naphthyl, a cycloalkyl, a monocyclic heterocyclic group, or a substituted or unsubstituted phenyl, which have excellent activities for alleviating, curing and preventing hepatic damages and are useful as a therapeutic or prophylactic agent for hepatic diseases, and processes for the preparation thereof, and a pharmaceutical composition containing the above compound as an active ingredient.

27 Claims, No Drawings

TETRAHYDRO-β-CARBOLINE DERIVATIVES AND TREATMENT OF LIVER DISEASES

This invention relates to novel tetrahydro-β-carboline derivatives of the formula:

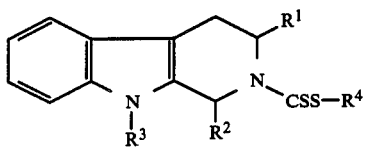

wherein
$R^1$ is carboxyl, a lower alkoxycarbonyl, carbamoyl, an N,N-di-lower alkylcarbamoyl, an N-(phenyl-substituted lower alkylidenamino)carbamoyl, a [N,N-di(lower alkyl)amino]-lower alkyl, or a nitrogen-containing monocyclic heterocyclic group;
$R^2$ is hydrogen atom, a lower alkyl, or a hydroxy-lower alkyl group; or
$R^2$ is combined with $R^1$ to form a group; —CO—O—CH$_2$—;
$R^3$ is hydrogen atom, a lower alkyl, a phenyl-lower alkyl, or a group of the formula: —CSS—R$^4$;
$R^4$ is hydrogen atom, an alkyl, or a group of the formula: —(CH$_2$)$_n$Y$^1$;
n is 0, 1 or 2,
$Y^1$ is a lower alkenyl, a phenyl-substituted lower alkenyl, an N,N-di(lower alkyl)amino, a lower alkylmercapto, a lower alkoxycarbonyl, benzoyl, naphthyl, a cycloalkyl, a monocyclic heterocyclic group, or a substituted or unsubstituted phenyl and a process for the preparation thereof.

This invention includes a pharmaceutically acceptable salt of the compounds of the formula (I) wherein $R^1$ is carboxyl, an N-(phenyl-substituted lower alkylidenamino)carbamoyl, a [N,N-di(lower alkyl)amino]-lower alkyl, or a nitrogen-containing monocyclic heterocyclic group, and of the compounds of the formula (I) wherein $R^4$ is hydrogen atom, or a group of the formula: —(CH$_2$)$_n$Y$^1$; n is 0, 1 or 2; and $Y^1$ is an N,N-di(lower alkyl)amino, a nitrogen-containing monocyclic heterocyclic group, or a phenyl substituted by carboxyl or amino.

The liver is an organ having various functions such as detoxication, carbohydrate metabolism, lipid metabolism, protein metabolism, production and secretion of bile, production of blood coagulation factors, control of hormones, regeneration of liver cells, storage of living body-constituting elements (e.g. fats, glycogen, proteins, vitamins), and the like. These functions are acutely or chronically affected by various disorders such as virus, drugs, poisons, alcohols, insufficient nutrition, vascular disfunction of the liver, obstruction of the bile duct, or the like. These liver function disorders appear clinically in the form of a viral hepatitis, drug-induced hepatopathy, alcoholic hepatitis, congestive hepatitis, hepatic disease caused by bile-congestion, fatty liver, jaundice, and finally hepatocirrhosis, or the like.

The novel tetrahydro-β-carboline derivatives of the formula (I) and a pharmaceutically acceptable salt thereof are useful as a therapeutic or prophylactic agent for hepatic disease because they exhibit excellent activities for alleviating or curing hepatic damages and also for protecting the liver from hepatic damages.

The tetrahydro-β-carboline derivatives of the present invention include compounds of the formula (I) wherein
$R^1$ is carboxyl; a lower alkoxycarbonyl such as methoxycarbonyl, ethoxycarbonyl, isopropoxycarbonyl, butoxycarbonyl; carbamoyl; an N,N-di(lower alkyl)carbamoyl such as N,N-dimethylcarbamoyl, N,N-diethylcarbamoyl; an N-(phenyl-substituted lower alkylidenamino)carbamoyl such as N-(benzylidenamino)-carbamoyl; a [N,N-di(lower alkyl)amino]-lower alkyl such as (N,N-dimethylamino)methyl, (N,N-dimethylamino)ethyl; or a nitrogen-containing monocyclic heterocyclic group such as tetrazolyl;
$R^2$ is hydrogen atom; a lower alkyl such as methyl, ethyl, n-propyl, n-butyl; or a hydroxy-lower alkyl group such as hydroxymethyl, hydroxyethyl, or
$R^2$ is combined with $R^1$ to form a group: —CO—O—CH$_2$—;
$R^3$ is hydrogen atom; a lower alkyl such as methyl, ethyl, propyl, butyl; a phenyl-lower alkyl such as benzyl, phenethyl; or a group of the formula: —CSS—R$^4$;
$R^4$ is hydrogen atom; an alkyl such as methyl, ethyl, propyl, butyl, pentyl, hexyl, heptyl, octyl, nonyl, decyl; or a group of the formula: —(CH$_2$)$_n$Y$^1$;
n is 0, 1 or 2,
$Y^1$ is a lower alkenyl such as vinyl, propenyl; a phenyl-substituted lower alkenyl such as styryl; an N,N-di(lower alkyl)amino such as N,N-dimethylamino, N,N-diethylamino; a lower alkylmercapto such as methylmercapto, ethylmercapto; a lower alkoxycarbonyl such as methoxycarbonyl, ethoxycarbonyl; benzoyl; naphthyl; a cycloalkyl such as cyclopentyl, cyclohexyl; a monocyclic heterocyclic group such as thienyl, furyl, pyridyl; phenyl; or a phenyl having one or two substituents selected from the group consisting of a halogen (e.g. chlorine, bromine, iodine, fluorine), amino, an N-acylamino (e.g. N-formylamino, N-acetylamino, N-benzyloxycarbonylamino), a lower alkoxy (e.g. methoxy, ethoxy, propoxy, butoxy), nitro, a lower alkyl (e.g. methyl, ethyl, propyl, butyl), carboxyl and a halogenated lower alkyl group (e.g. trifluoromethyl).

Preferred compounds are compounds of the formula (I) wherein
$R^1$ is carboxyl, methoxycarbonyl, ethoxycarbonyl, isopropoxycarbonyl, carbamoyl, N,N-dimethylcarbamoyl, N-(benzylidenamino)carbamoyl, (N,N-dimethylamino)methyl or tetrazolyl,
$R^2$ is hydrogen atom, methyl, ethyl, n-propyl, n-butyl or hydroxymethyl, or
$R^2$ is combined with $R^1$ to form a group: —CO—O—CH$_2$—,
$R^3$ is hydrogen atom, methyl, benzyl, or a group of the formula: —CSS—R$^4$,
$R^4$ is a hydrogen atom, methyl, ethyl, n-propyl, n-butyl, n-decyl or a group of the formula: —(CH$_2$)$_n$Y$^1$,
n is 0, 1 or 2, and
$Y^1$ is vinyl, styryl, N,N-dimethylamino, methylmercapto, ethoxycarbonyl, benzoyl, naphthyl, cyclohexyl, thienyl, furyl, pyridyl, phenyl, or a phenyl having one to two substituent(s) selected from the group consisting of chlorine, amino, benzyloxycarbonylamino, formylamino, methoxy, nitro, methyl, carboxyl and trifluoromethyl.

More preferred compounds are compounds of the formula (I) wherein
- R¹ is carboxyl, methoxycarbonyl, ethoxycarbonyl, carbamoyl, N,N-dimethylcarbamoyl, (N,N-dimethylamino)methyl or tetrazolyl,
- R² is a hydrogen atom, methyl, ethyl, n-propyl or hydroxymethyl,
- R³ is a hydrogen atom, methyl, benzyl, or a group of the formula: —CSS—R⁴,
- R⁴ is hydrogen, methyl, ethyl, n-propyl, allyl, cinnamyl, 2-thenyl, benzyl, 4-chlorobenzyl, 4-aminobenzyl, 4-(benzyloxycarbonylamino)benzyl, 4-(formylamino)benzyl, 4-methoxybenzyl or 4-methylbenzyl.

Further preferred compounds are compounds of the fromula (I) wherein
- R¹ is carboxyl, methoxycarbonyl, N,N-dimethylcarbamoyl, (N,N-dimethylamino)methyl or tetrazolyl,
- R² is a hydrogen atom, methyl, ethyl, n-propyl or hydroxymethyl,
- R³ is a hydrogen atom or a group:

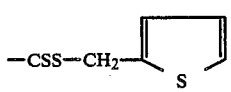

R⁴ is a hydrogen atom, methyl, ethyl, 2-thenyl or 4-aminobenzyl.

Still further preferred compounds are compounds of the formula (I) wherein R¹ is carboxyl, R² is a hydrogen atom, methyl or hydroxymethyl, R³ is a hydrogen atom and R⁴ is methyl.

The compounds of the formula (I) wherein R¹ is carboxyl, an N-(phenyl-substituted lower alkylidenamino)carbamoyl, a [N,N-di(lower alkyl)amino]-lower alkyl, or a nitrogen-containing monocyclic heterocyclic group, and the compounds of the formula (I) wherein R⁴ is a hydrogen atom, or a group of the formula: —(CH$_2$)$_n$Y¹; n is 0, 1 or 2; and Y¹ is an N,N-di(lower alkyl)amino, a nitrogen-containing monocyclic heterocyclic group, or a phenyl substituted by carboxyl or amino, may be used in the form of a pharmaceutically acceptable salt thereof. In case wherein R¹ is carboxyl or R⁴ is hydrogen atom or a group of the formula: —(CH$_2$)$_n$Y¹; and Y¹ is a phenyl substituted by carboxyl, suitable examples of the salt are an alkali metal salt (e.g., sodium or potassium salt), an organic amine salt (e.g., triethylamine, trimethylamine, N-methylmorpholine or dicyclohexylamine salt), and the like. When R¹ is an N-(phenyl-substituted lower alkylidenamino)carbamoyl, a [N,N-di(lower alkyl)amino]-lower alkyl or a nitrogen-containing monocyclic heterocyclic group, or when R⁴ is a group of the formula: —(CH$_2$)$_n$Y¹ and Y¹ is an N,N-di(lower alkyl)amino, a nitrogen-containing monocyclic heterocyclic group or a phenyl substituted by amono, suitable examples of the salt are a mineral acid salt (e.g., hydrochloride, sulfate), an aromatic sulfonate (e.g., benzenesulfonate, toluenesulfonate), an alkylsulfonate (e.g., methanesulfonate, ethanesulfonate), and the like.

The compounds of the formula (I) wherein R² is a hydrogen atom include two optical isomers and a racemic mixture. Besides, the compounds of the formula (I) wherein R² is a lower alkyl group or a hydroxy-lower alkyl group, include two stereoisomers (i.e. cis- and trans-isomers), and each stereoisomer includes further two optical isomers and a racemic mixture. Moreover, the compounds of the formula (I) wherein R¹ and R² combine together to form a group: —CO—O—CH$_2$— has cis-configuration, which includes further two optical isomers and a racemic mixture. The present invention includes within its scope these isomers and a mixture thereof.

According to the present invention, the compounds (I) can be prepared by the following processes.

PROCESS A

The compound (I) can be prepared by reacting a compound of the formula:

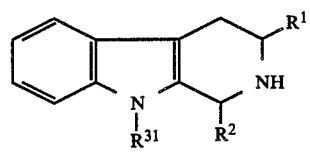

wherein R³¹ is hydrogen atom, a lower alkyl, or a phenyl-lower alkyl group, and R¹ and R² are as defined above, with carbon disulfide, or with carbon disulfide and a compound of the formula:

$$R^{41}-X^1 \quad \text{(III)}$$

wherein R⁴¹ is an alkyl or a group of the formula: —(CH$_2$)$_n$Y¹, n is 0, 1 or 2, Y¹ is a lower alkenyl, a phenyl-substituted lower alkenyl, an N,N-di(lower alkyl)amino, a lower alkylmercapto, a lower alkoxycarbonyl, benzoyl, naphthyl, a cycloalkyl, a monocyclic heterocyclic group, or a substituted or unsubstituted phenyl, and X¹ is a reactive residue.

PROCESS B

A compound of the formula:

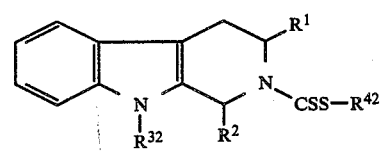

wherein R³² is hydrogen atom, a lower alkyl, a phenyl-lower alkyl, or a group of the formula: —CSS—R⁴², R⁴² is a group of the formula: —(CH$_2$)$_n$Y², n is 0, 1 or 2, Y² is a phenyl substituted by amino group, and R¹ and R² are as defined above, can be prepared by deacylating a compound of the formula:

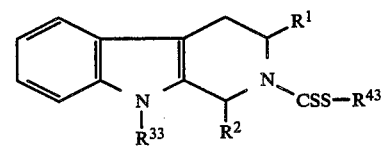

wherein R³³ is hydrogen atom, a lower alkyl, a phenyl-lower alkyl, or a group of the formula: —CSS—R⁴³, R⁴³ is a group of the formula: —(CH$_2$)$_n$Y³, n is 0, 1 or 2, Y³ is a phenyl substituted by an N-acylamino group, and R¹ and R² are as defined above.

PROCESS C

A compound of the formula:

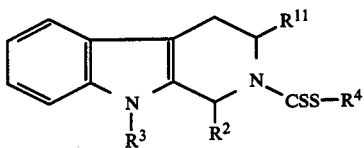

wherein $R^{11}$ is carboxyl group and $R^2$, $R^3$ and $R^4$ are as defined above, can be prepared by hydrolyzing a compound of the formula:

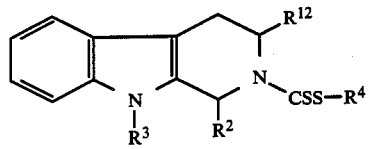

wherein $R^{12}$ is a lower alkoxycarbonyl group, and $R^2$, $R^3$ and $R^4$ are as defined above.

PROCESS D

The compound of the formula (I-d) can also be prepared by esterifying a compound of the formula (I-c).

Preferred starting compound (III) is a compound of the formula (III) wherein $X^1$ is a halogen such as chlorine, bromine, iodine or fluorine, or a diazonium residue of the formula: $-N_2X^2$ ($X^2$ is a halogen).

The processes are explained in more detail below.

(Process A)

The reaction of the compound (II) with carbon disulfide and the reaction of the compound (II), carbon disulfide and the compound (III) are carried out in a solvent in the presence of a base. The base includes alkali metal hydroxides (e.g. sodium hydroxide, potassium hydroxide), and organic amines (e.g. trimethylamine, triethylamine, N-methylmorpholine, dicyclohexylamine). Suitable examples of the solvent are water, methanol, ethanol, dimethylsulfoxide, tetrahydrofuran, dioxane, dimethylformamide, or a mixture thereof. The reaction temperature is in the range of 0° to 50° C., preferably 10° to 30° C.

(Process B)

The deacylation of the compound (I-b) can be carried out under the conditions suitable thereto according to the kinds of the acyl groups thereof. Examples of the acyl group include lower aliphatic acyl group such as formyl or acetyl, or aralkyloxycarbonyl such as benzyloxycarbonyl. For example, in the case of a compound (I-b) wherein $Y^3$ is a lower aliphatic acylamino-substituted phenyl group such as N-formylamino-substituted phenyl group, the compound is treated with thioglycolic acid and 6N HCl in ethanol at 0° to 50° C. In the case of a compound (I-b) wherein $Y^3$ is a aralkyloxycarbonylamino-substituted phenyl group such as N-benzyloxycarbonyl-amino-substituted phenyl group, the compound is reduced in the presence of a catalyst (e.g. Pd-C, or Pt) in a solvent (e.g. methanol, ethanol, ethyl acetate, tetrahydrofuran, water, or a mixture of these solvents).

(Process C)

The hydrolysis of the compound (I-d) can be carried out by treating it with an acid or an alkali, preferably with an alkali, in a solvent. Suitable examples of the solvent are water, methanol, ethanol, dimethoxyethane, or a mixture of these solvents. The acid includes mineral acids such as hydrochloric acid, or sulfuric acid, and the alkali includes alkali metal hydroxides such as sodium hydroxide, or potassium hydroxide. The reaction is preferably carried out at a temperature of from 0° to 50° C.

(Process D)

The esterification of the compound (I-c) can be carried out by various methods.

For example, the esterification is carried out by reacting a reactive derivative of a compound (I-c) with an alkanol of the formula: $R^{13}OH$ (wherein $R^{13}$ is a lower alkyl group). The reactive derivative includes, for example, an acid halide, such as acid chloride or acid bromide. The alkanol includes preferably a compound of the formula: $R^{13}OH$ wherein $R^{13}$ is methyl, ethyl, n-propyl, or isopropyl. The reaction of an acid halide of a compound (I-c) with an alkanol is carried out in a solvent in the presence or absence of an acid acceptor. The acid acceptor includes organic bases such as triethylamine, tributylamine or pyridine, and inorganic bases such as potassium carbonate, sodium carbonate, or sodium hydrogen carbonate. The solvent includes, for example, methylene chloride, chloroform, carbon tetrachloride, tetrahydrofuran, dioxane, acetonitrile, benzene, toluene, dimethylformamide, or the like. When an alkanol is used in an excess amount, it can also serve as a solvent, and hence, additional solvent is not necessarily required. The reaction is usually carried out at a temperature of from $-10°$ to 60° C., preferably $-10°$ to 30° C.

The acid halide of a compound (I-c) is usually prepared by reacting a free carboxylic acid of the formula (I-c) or a salt thereof (e.g. an alkali metal salt such as sodium or potassium salt, a tertiary amine salt such as triethylamine or tributylamine salt) with a halogenating agent (e.g., thionyl chloride, oxalyl chloride, phosphorus oxychloride, phosphorus trichloride, phosphorus tribromide) in a solvent (e.g., benzene, toluene, chloroform, dioxane, tetrahydrofuran, acetonitrile). When a halogenating agent is used in an excess amount, it can also serve as a solvent, and hence, additional solvent is not necessarily required. The halogenation reaction is preferably carried out at a temperature of from $-10°$ to 60° C.

The esterification of a compound (I-c) can also be carried out by reacting a compound (I-c) with an alkanol ($R^{13}OH$). This reaction is usually carried out by dissolving a compound (I-c) in an excess amount of an alkanol, introducing thereof gaseous hydrochloric acid, preferably at a temperature of from 0° to 10° C., and then heating the mixture at a reflux temperature.

A compound of the formula (I-d) wherein $R^{12}$ is lower alkoxycarbonyl group is also prepared by reacting a compound (I-c) with diazoalkane (e.g., diazomethane, diazoethane) in a solvent such as ether, ethyl acetate, or dimethoxyethane, preferably at a temperature of $-10°$ to 10° C. The diazoalkane is preferably used in the form of a solution in ether.

A compound of the formula (I) wherein $R^1$ and $R^2$ combine to form a group: $-CO-O-CH_2-$ can be prepared from the corresponding compound (II) (i.e. a compound of the formula (II) wherein $R^1$ and $R^2$ combine to form a group: $-CO-O-CH_2-$), but may also directly be prepared from a compound of the formula (II) wherein $R^1$ is carboxyl group and $R^2$ is hydroxymethyl group. The reaction is readily carried out under the same conditions as Process A.

Among the desired compound (I) thus prepared, the compound of the formula (I) wherein $R^1$ is carboxyl, an N-(phenyl-substituted lower alkylidenamino)carbamoyl, a [N,N-di(lower alkyl)amino]-lower alkyl, or a nitrogen-containing monocyclic heterocyclic group, and the compound of the formula (I) wherein $R^4$ is hydrogen atom, or a group of the formula: —$(CH_2)_nY^1$; n is 0, 1 or 2; and $Y^1$ is an N,N-di(lower alkyl)amino, a nitrogen-containing monocyclic heterocyclic group, or a phenyl substituted by carboxyl or amino, are optionally converted into a pharmaceutically acceptable salt thereof, which can be obtained by treating the free compound with an acid or an alkali in a usual manner.

The above reactions can proceed without racemization, and hence, when an optical active compound is used as the starting compound, the desired compounds are also obtained in an optically active form.

The starting compounds (II) can be prepared, for example, by the processes of the following reaction schemes:

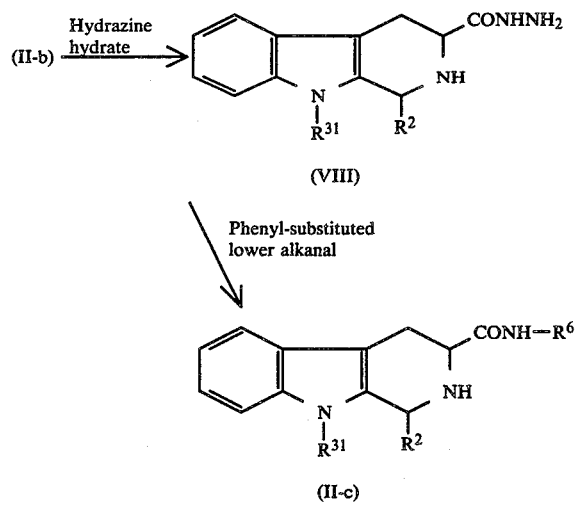

Process (ii)

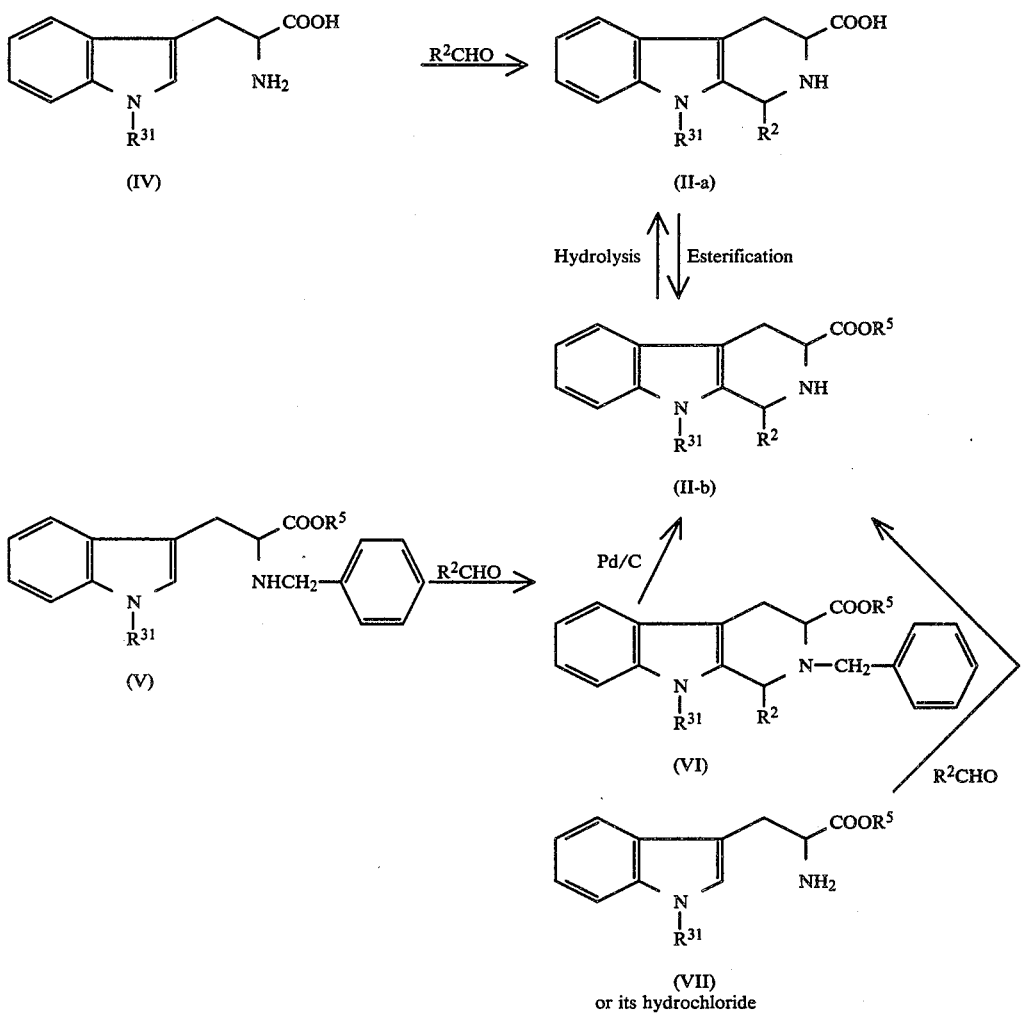

Process (i)

Process (iii)

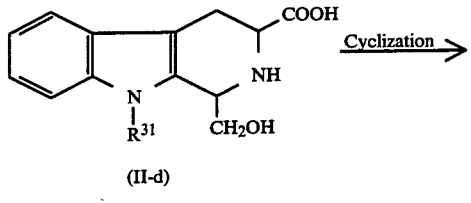

(II-d)

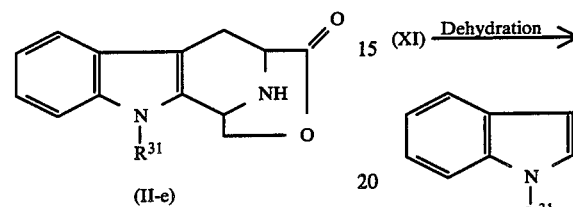

(II-e)

Process (iv)

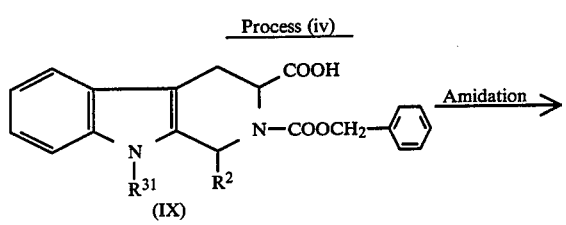

(IX)

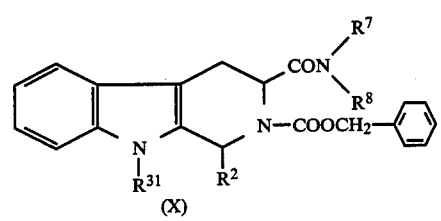

(X)

↓ Catalytic reduction

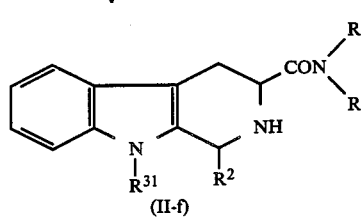

(II-f)

Process (v)

(IX) 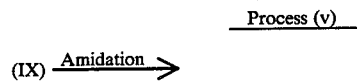

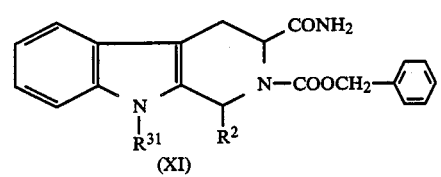

(XI)

↘ Catalytic reduction

-continued
Process (v)

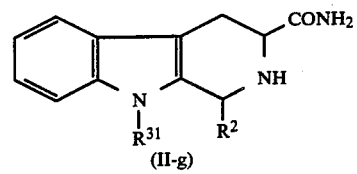

(II-g)

Process (vi)

(XI) — Dehydration →

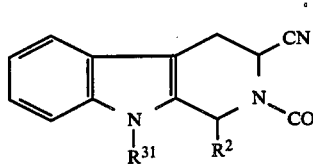

(XII)

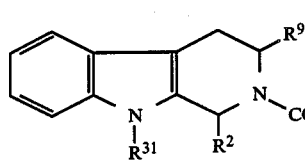

(XIII) 

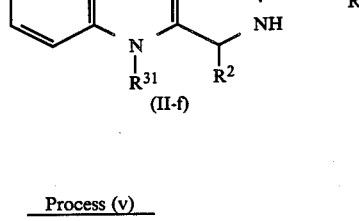

(II-h)

wherein $R^5$ is a lower alkyl, $R^6$ is a phenyl-substituted lower alkylidenamino, $R^7$ and $R^8$ are each a lower alkyl, $R^9$ is a nitrogen-containing monocyclic heterocyclic group, and $R^2$ and $R^{31}$ are as defined above.

According to Process (i), the starting compounds (II-a) and (II-b), i.e. the compound (II) wherein $R^1$ is carboxyl or a lower alkoxycarbonyl group, can be prepared by well known processes, for example, as disclosed in J. Med. Chem., 16, 418 (1973); J. Med. Chem., 16, 560 (1973); J. Med. Chem., 25, 1081 (1982); and J. Am. Chem. Soc., 102, 6976 (1980).

According to Process (ii), the starting compound (II-c), i.e. the compound (II) wherein $R^1$ is an N-(phenyl-substituted lower alkylidenamino)carbamoyl group, can be prepared by reacting a compound (II-b) with hydrazine hydrate in a solvent (e.g. dimethylformamide, methanol, ethanol, dioxane) at room temperature, and reacting the resulting acid hydrazide compound (VIII) with a phenyl-substituted lower alkanal in a solvent (e.g. dimethylsulfoxide, dimethylformamide) at room temperature. The compound (II-c) thus obtained can be used as it stands, i.e. without isolating from the reaction mixture.

According to Process (iii), the starting compound (II-e), i.e. the compound (II) wherein $R^1$ and $R^2$ are combined to form a group: —CO—O—CH$_2$—, can be prepared by subjecting a compound (II-d) to a cyclization reaction. The cyclization reaction is usually carried out by heating the compound (II-d) in a solvent (e.g. chloroform, benzene, toluene) in the presence or absence of an acid (e.g. hydrochloric acid, p-toluenesulfonic acid).

According to Process (iv), the starting compound (II-f), i.e. the compound (II) wherein R$^1$ is an N,N-di(-lower alkyl)carbamoyl group, can be prepared, for example, by reacting a compound (IX) with a lower alkylamine or its hydrochloride in a solvent (e.g. tetrahydrofuran, dioxane dimethylformamide), in the presence of a dehydrating agent (e.g. N,N'-dicyclohexylcarbodiimide, 1-ethyl-3-(3-dimethylaminopropyl)carbodiimide) and also in the presence of triethylamine and 1-hydroxybenzotriazole at a temperature of from 0° to 50° C. to prepare a compound (X), and then reducing the resulting compound (X) in a solvent (e.g. methanol, ethanol, ethyl acetate, tetrahydrofuran, acetic acid, water, or a mixture of these solvents) in the presence of a catalyst (e.g. Pd-C, Pt).

According to Process (v), the starting compound (II-g), i.e. the compound (II) wherein R$^1$ is carbamoyl group, can be prepared, for example, by reacting a compound (IX) with ethyl chlorocarbonate in a solvent (e.g. ethyl acetate, tetrahydrofuran, chloroform, dimethylformamide) in in the presence of a catalyst (e.g. triethylamine, N-methylmorpholine) under cooling (e.g. at −20° to 0° C.), and then adding aqueous ammonia to the reaction mixture to give a compound (XI), and then catalitically reducing the resulting compound (XI).

The starting compound (II) wherein R$^1$ is a nitrogen-containing monocyclic heterocyclic group can be prepared according to Process (vi). For example, a compound (II-h) wherein R$^9$ is tetrazolyl, i.e. the compound (II) wherein R$^1$ is tetrazolyl, can be prepared by treating a compound (XI) with a dehydrating agent (e.g. POCl$_3$, phosphorus pentoxide, benzenesulfonyl chloride) in a solvent (e.g. pyridine, acetonitrile) to prepare a nitrile compound (XII), treating the resulting compound (XII) with NaN$_3$ and NH$_4$Cl in a solvent (e.g. dimethylformamide, dimethylacetamide, dimethylsulfoxide) with heating (e.g. at 90° to 100° C.) to prepare a compound (XIII), and then treating the compound (XIII) with HBr in a solvent (e.g. acetic acid, water).

The starting compound (II) wherein R$^1$ is a [N,N-di(-lower alkyl)amino]-lower alkyl group can be prepared by reducing the corresponding 3-[N,N-di(lower alkyl)amino]-lower alkanoyl-1,2,3,4-tetrahydro-$\beta$-carboline compound in a solvent (e.g., tetrahydrofuran, dioxane, dimethoxyethane) with a reducing agent (e.g. LiAlH$_4$, diborane).

The starting compound (IX) used in the above Processes (iv) and (v) can be prepared by a process as disclosed, for example, in Chem. Pharm. Bull., 25, 1559 (1977).

There are known a variety of causal factors inducing toxic liver damage, hepatitis and fatty liver. The predominant changes observed in these diseases are necrosis of liver cells, mesenchymal reaction and accumulation of lipid. The feature of necrosis depends on the causal factor and it can be classified into centrilobular necrosis, periportal necrosis and discrete lobular necrosis. In experimentation, the centrilobular necrosis is induced by carbon tetrachloride, and the degree of liver damage is determined by the measurement of liver weight and observation of the liver color with the naked eye. The periportal necrosis and the discrete lobular necrosis associated with mesenchymal reaction are induced by allyl alcohol and D-galactosamine, respectively, and the degree of liver damage is determined by the measurement of activities of glutamic-pyruvic-transaminase (GPT) and glutamic-oxaloacetic-transaminase (GOT) in the blood plasma.

The compounds (I) of the present invention have excellent activities for curing, preventing and alleviating various liver diseases, particularly liver diseases associated with centrilobular necrosis, liver diseases associated with periportal necrosis, liver diseases associated with discrete lobular necrosis and mesenchymal reaction, fatty liver, drug-induced hepatopathy, and congestive hepatitis. Accordingly, the compounds (I) of the present invention are useful as a therapeutic or prophylactic agent for hepatic diseases in animals including human, and are used, for example, for treating or preventing various diseases such as viral hepatitis, drug-induced hepatopathy, alcoholic hepatitis, fatty liver, jaundice, and also the final symptom, i.e. hepatocirrhosis. Moreover, the compounds of the present invention also show stimulation of the liver function with low toxicity and hence with high safety. For example, when the present compounds, (3RS)-2-dithiocarboxy-1,2,3,4-tetrahydro-$\beta$-carboline-3-carboxylic acid disodium salt, (3R)-2-[(methylthio)thiocarbonyl]-1,2,3,4-tetrahydro-$\beta$-carboline-3-carboxylic acid, (3S)-2-[(methylthio)thiocarbonyl]-1,2,3,4-tetrahydro-$\beta$-carboline-3-carboxylic acid, or (3RS)-2-[(methylthio)thiocarbonyl]-1,2,3,4-tetrahydro-$\beta$-carboline-3-carboxylic acid were orally administered to mice in a dose of 1,500 mg/kg, no mice died during 7 days-observation after the administration. Further, the compounds (I) of the present invention have an activity of inhibiting undesirable production of lipid peroxides. Lipid peroxide levels in tissues of mammalian species are known to increase with age and cause cell death and/or damage with a consequent change of cell permeability. In addition, lipid peroxides have been suggested to be a primary etiologic factor in the genesis of stroke (cf. Stroke, Vol. 10, No. 3, pages 323–326 (1979). Thus, the compounds (I) may be used to improve the lipid peroxide levels in the tissues of the aged subjects.

When the compounds (I) and their salts of the present invention are used as a medicine, they can be administered by an oral route or a parenteral route (e.g. intraveneous, intramuscular or subcutaneous route). The dose of the compounds (I) and their salts may vary according to ages, weights and states of patients, severity of diseases, or the like, but is usually in the range of about 0.01 to 250 mg/kg/day, preferably 0.1 to 50 mg/kg/day. Particularly preferred doses of the present compounds (I) in the case of oral administration are in the range of about 0.1 to 250 mg/kg/day, especially 0.5 to 50 mg/kg/day.

The compounds (I) and their salts can be used in the form of conventional pharmaceutical preparations in admixture with conventional pharmaceutical carriers or diluents which are usually used for oral or parenteral preparations. The carriers include, for example, gelatine, lactose, glucose, sodium chloride, starch, magnesium stearate, talc, vegetable oils, and the like. The pharmaceutical preparations may be solid preparations such as tablets, sugar coating tablets, pills, capsules or powders, or liquid preparations such as solutions, suspensions, or emulsions. These preparations may be sterilized. Moreover, various auxiliaries, stabilizers, wetting agents, emulsifiers, or any other additives may optionally be added to the preparations.

The present invention is illustrated by the following Experiments and Examples, but it should not be construed to be limited thereto.

Throughout the specification and claims, the terms "lower alkyl", "lower alkoxy", "lower alkenyl", "cycloalkyl", "alkyl" "lower alkanal" and "lower alkanoyl" should be interpreted as referring to alkyl of one to four carbon atoms, alkoxy of one to four carbon atoms, alkenyl of two to four carbon atoms, cycloalkyl of three to seven carbon atoms, alkyl of one to ten carbon atoms, alkanal of one to four carbon atoms, and alkanoyl of one to four carbon atoms, respectively.

As is shown in the following formulae, the compound (I) wherein $R^1$ is tetrazolyl has two tautomeric structures which are mutually convertible from one to another. Both of these isomers are included in the present invention.

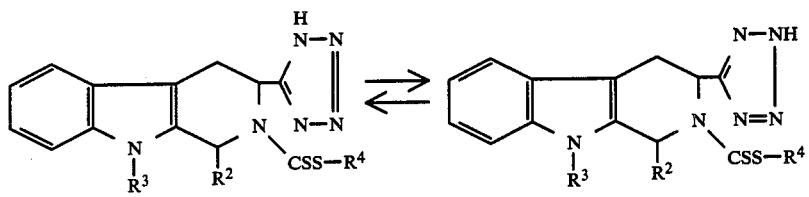

EXPERIMENT 1

Protection against acute hepatic damage induced by carbon tetrachloride:

Method: The test compounds were suspended in 0.5% carboxymethyl cellulose solution, and the suspension (test compound: 100 mg/10 ml/kg) was orally administered to ddY male mice (age: 5-6 weeks old, weight: 25-30 g, one group: 3 mice) and the animals were fasted. After 3 hours, a solution of carbon tetrachloride in olive oil was orally administered in a dose of 50 μl/5 ml olive oil/kg. After 3 hours, the test compound was again orally administered in the same dose as above. Weight of the animals was measured 24 hours after CCl$_4$ administration, and then, the animals were killed. Immediately, the liver was taken out, weighed and macroscopically observed. As the normal control, 0.5% carboxymethyl cellulose solution and olive oil were orally administered to the animals instead of the suspension of the test compound and the CCl$_4$ solution. Besides, the CCl$_4$-control group was given the CCl$_4$ solution and 0.5% carboxymethyl cellulose solution.

The therapeutic effect of the test compounds on liver damages was evaluated based on the suppressive % of the increase of relative liver weight calculated by the following equation and also based on the macroscopic observation of the liver, as shown in Table 1. The term "relative liver weight" means weight (g) of the liver/100 g body weight.

Suppressive % of the increase of relative liver weight =

$$\left[ 1 - \frac{\begin{array}{c}\text{Mean of relative} \\ \text{liver weight in} \\ \text{test compound} \\ \text{group}\end{array} - \begin{array}{c}\text{Mean of relative} \\ \text{liver weight in} \\ \text{normal control} \\ \text{group}\end{array}}{\begin{array}{c}\text{Mean of relative} \\ \text{liver weight in} \\ \text{CCl}_4\text{-control} \\ \text{group}\end{array} - \begin{array}{c}\text{Mean of relative} \\ \text{liver weight in} \\ \text{normal control} \\ \text{group}\end{array}} \right] \times 100$$

TABLE 1

| Macroscopic observation of the liver | (Criteria) Suppressive % of the increase of relative liver weight | | |
|---|---|---|---|
| | ≧20% | ≧−20% to <20% | <−20% |
| Almost the same as normal control group | AA | C | D |
| Showed a sign of amelioration from CCl$_4$—control group | A | C | D |
| Showed the same color or appearance as in CCl$_4$—control group | B | D | D |

Remarks: AA means "significantly effective", A, B and C mean "effective", and D means "not effective"

The results of the above experiment are shown in the following Table 2.

TABLE 2

| Test compound Nos. and chemical name | Evaluation (Dose: 100 mg/kg × 2) |
|---|---|
| 1. (3RS)-2-Dithiocarboxy-1,2,3,4-tetrahydro-β-carboline-3-carboxylic acid disodium salt | AA |
| 2. (3R)-2-[(Methylthio)thiocarbonyl]-1,2,3,4-tetrahydro-β-carboline-3-carboxylic acid | AA |
| 3. (3S)-2-[(Methylthio)thiocarbonyl]-1,2,3,4-tetrahydro-β-carboline-3-carboxylic acid | AA |
| 4. (3RS)-2-[(Methylthio)thiocarbonyl]-1,2,3,4-tetrahydro-β-carboline-3-carboxylic acid | AA |
| 5. (3RS)-2-[(Methylthio)thiocarbonyl]-1,2,3,4-tetrahydro-β-carboline-3-carboxylic acid sodium salt | AA |
| 6. (3RS)-2-[(Ethylthio)thiocarbonyl]-1,2,3,4-tetrahydro-β-carboline-3-carboxylic acid | AA |
| 7. (3R)-2-[(4-Aminobenzylthio)thiocarbonyl]-1,2,3,4-tetrahydro-β-carboline-3-carboxylic acid | AA |
| 8. (3R)-2-[(2-Thenylthio)thiocarbonyl]-1,2,3,4-tetrahydro-β-carboline-3-carboxylic acid | AA |
| 9. (3S)-2-[(2-Thenylthio)thiocarbonyl]-1,2,3,4-tetrahydro-β-carboline-3-carboxylic acid | AA |
| 10. (3RS)-2-[(2-Thenylthio)thiocarbonyl]-1,2,3,4-tetrahydro-β-carboline-3-carboxylic acid | AA |
| 11. (1S, 3S)-1-Methyl-2-[(methylthio)thiocarbonyl]-1,2,3,4-tetrahydro-β-carboline-3-carboxylic acid | AA |
| 12. (1RS, 3RS)-cis-1-Ethyl-2-[(methylthio)thiocarbonyl]-1,2,3,4-tetrahydro-β-carboline-3-carboxylic acid | AA |

TABLE 2-continued

| Test compound Nos. and chemical name | Evaluation (Dose: 100 mg/kg × 2) |
|---|---|
| 13. (1RS, 3SR)-trans-1-Ethyl-2-[(methylthio)thiocarbonyl]-1,2,3,4-tetrahydro-β-carboline-3-carboxylic acid | AA |
| 14. (3R)-2,9-Di[(2-thenylthio)thiocarbonyl]-1,2,3,4-tetrahydro-β-carboline-3-carboxylic acid | AA |
| 15. Methyl (3RS)-2-[(methylthio)thiocarbonyl]-1,2,3,4-tetrahydro-β-carboline-3-carboxylate | AA |
| 16. Methyl (3S)-2-[(2-thenylthio)thiocarbonyl]-1,2,3,4-tetrahydro-β-carboline-3-carboxylate | AA |
| 17. Methyl (1S, 3S)-1-methyl-2-[(methylthio)thiocarbonyl]-1,2,3,4-tetrahydro-β-carboline-3-carboxylate | AA |
| 18. (3RS)-2-[(Methylthio)thiocarbonyl]-1,2,3,4-tetrahydro-β-carboline-3-N,N—dimethylcarboxamide | AA |
| 19. Methyl (3RS)-3-(N,N—dimethylamino)methyl-1,2,3,4-tetrahydro-β-carboline-2-carbodithioate hydrochloride | AA |
| 20. Methyl (3RS)-3-(1H—tetrazol-5-yl)-1,2,3,4-tetrahydro-β-carboline-2-carbodithioate | AA |
| 21. (1RS, 3RS)-cis-1-n-Propyl-2-[(methylthio)thiocarbonyl]-1,2,3,4-tetrahydro-β-carboline-3-carboxylic acid | AA |
| 22. (1RS, 3SR)-trans-1-n-Propyl-2-[(methylthio)-thiocarbonyl]-1,2,3,4-tetrahydro-β-carboline-3-carboxylic acid | AA |
| 23. (1RS, 3RS)-cis-1-Hydroxymethyl-2-[(methylthio)thiocarbonyl]-1,2,3,4-tetrahydro-β-carboline-3-carboxylic acid | AA |

EXPERIMENT 2

Protection against acute hepatic damage induced by allyl alcohol:

Method: The test compounds were suspended in 0.5% carboxymethyl cellulose solution, and the suspension (test compound: 100 mg/10 ml/kg) was orally administered to ddY male mice (age: 6 weeks old, weight: 27-31 g, one group: 6 mice) and the animals were fasted. After 3 hours, a solution of allyl alcohol in olive oil was orally administered in a dose of 75 μl/5 ml olive oil/kg. After 3 hours, the test compound was again orally administered in the same dose as above. 24 hours after the administration of allyl alcohol, blood was collected by cutting the carotid artery and was centrifuged to isolate blood plasma. Activity of GPT (glutamic-pyruvic-transaminase) in the blood plasma were measured, and the data were expressed by Karmen unit (K.U.). As the normal control, 0.5% carboxymethyl cellulose solution and olive oil were orally administered to the animals instead of the suspension of the test compound and the allyl alcohol solution. Besides, the allyl alcohol control group was given the allyl alcohol solution and 0.5% carboxymethyl cellulose solution.

The test results are shown in the following table 3.

TABLE 3

| | Test compound group Test compound No. 2* | Allyl alcohol control group | Normal control group |
|---|---|---|---|
| GPT (K.U.) | 553 ± 64 | 913 ± 157 | 14 ± 2 |

*Test compound No. 2: The same as used in Experiment 1

EXPERIMENT 3

Activity against acute hepatic damage induced by galactosamine:

Method: The test compounds were suspended in 0.5% carboxymethyl cellulose solution, and the suspension (test compound: 300 mg/10 ml/kg) was orally administered to fasted Wistar male rats (age: 9 weeks old, weight: 190-220 g, one group: 5 rats). After 24 hours, a solution of D-galactosamine in physiological saline solution was intraperitoneally administered in a dose of 400 mg/10 ml saline solution/kg. After 24 hours, the test compound was again orally administered in the same dose as above. 48 hours after administration of D-galactosamine, blood was collected from the axillary vein. The plasma was isolated from the blood, and activities of GPT and GOT (glutamic-oxaloacetic-transaminase) in the plasma were measured. As the normal control, 0.5% carboxymethyl cellulose solution and physiological saline solution were administered to the animals instead of the suspension of the test compound and the D-galactosamine solution. Besides, the D-galactosamine control group was given the D-galactosamine solution and 0.5% carboxymethyl cellulose solution.

The test results are shown in the following table 4.

TABLE 4

| | Test compound group Test compound No. 4* | D-galactosamine control group | Normal control group |
|---|---|---|---|
| GPT (K.U.) | 20.7 ± 1.3 | 41.7 ± 7.7 | 18.3 ± 1.3 |
| GOT (K.U.) | 242 ± 7.6 | 380 ± 44.3 | 65 ± 8.7 |

*Test compound No. 4: The same as used in Experiment 1

EXPERIMENT 4

(Preventive effect on lipid peroxide formation)

0.1 ml of a dimethylsulfoxide solution containing $3 \times 10^{-3}$M of a test compound was added to a mixture of 2.4 ml of 0.067M potassium phosphate buffer solution (pH 7.4) and 0.5 ml of 10% rat brain-homogenate (final concentration of the test compound: $10^{-4}$M). After a one-hour incubation of the mixture at 37° C., one ml of 20% trichloroacetic acid was added thereto, and lipid peroxide formations were determined by the thiobarbituric acid colorimetric method (J. Robak et al., Biochem. Pharmacol., Vol. 25, page 2233 (1976)). Percentage inhibition of lipid peroxide formation of the test compound was calculated according to the following equation:

$$\text{Inhibitory \% of lipid peroxide formation} = \left[1 - \frac{\Delta OD \text{ of test tube*}}{\Delta OD \text{ of control tube**}}\right] \times 100$$

Note:
*tube containing the test compound
**tube containing an equal volume of dimethylsulfoxide instead of the test compound solution
ΔOD was calculated as [(optical density measured at 532 nm) − (optical density measured at 600 nm)]

The results are shown in the following Table 5.

TABLE 5

| Test compound Nos.* | Inhibitory % of lipid peroxide formation |
|---|---|
| 7 | 98.4 |
| 9 | 95.8 |
| 14 | 95.3 |
| 15 | 81.5 |
| 16 | 82.6 |
| 24 | 97.4 |
| 25 | 92.1 |

TABLE 5-continued

| Test compound Nos.* | Inhibitory % of lipid peroxide formation |
|---|---|
| 26 | 73.6 |

*Test compound Nos. 7, 9, 14 to 16: The same as used in Experiment 1
Test compound No. 24: Ethyl (3R)-2-[(methylthio)thiocarbonyl]-1,2,3,4-tetrahydro-β-carboline-3-carboxylate
Test compound No. 25: Ethyl (3S)-2-[(methylthio)thiocarbonyl]-1,2,3,4-tetrahydro-β-carboline-3-carboxylate
Test compound No. 26: Methyl (3R)-2,9-di[(2-thenylthio)thiocarbonyl]-1,2,3,4-tetrahydro-β-carboline-3-carboxylate

EXAMPLE 1

(3RS)-2-Dithiocarboxy-1,2,3,4-tetrahydro-β-carboline-3-carboxylic acid disodium salt To a mixture of (3RS)-1,2,3,4-tetrahydro-β-carboline-3-carboxylic acid (2.16 g), 1N NaOH (20.3 ml), ethanol (10 ml) and water (20 ml) is added dropwise carbon disulfide (0.84 g). The mixture is stirred under ice-cooling for one hour. The reaction mixture is distilled under reduced pressure to remove the solvent. The residue is dissolved in ethanol, and the undissolved materials are filtered off. The filtrate is concentrated under reduced pressure to give the title compound (3.2 g, 92%) as powder.

IR $\nu_{max}^{nujol}$ (cm$^{-1}$): 1590.

EXAMPLE 2

(3R)-2-[(Methylthio)thiocarbonyl]-1,2,3,4-tetrahydro-β-carboline-3-carboxylic acid (i) To a mixture of (3R)-1,2,3,4-tetrahydro-β-carboline-3-carboxylic acid (6.49 g), KOH (3.5 g) and 50% ethanol (110 ml) is added dropwise carbon disulfide (1.82 ml) under ice-cooling. The mixture is stirred at room temprature for one hour, and thereto is added dropwise methyl iodide (2.5 ml). The mixture is further stirred at room temperature for 4 hours. The reaction mixture is distilled to remove the solvent. The residue is dissolved in water. The solution is acidified with 10% HCl and extracted with ethyl acetate. The extract is washed with water, dried and distilled to remove the solvent. The residue is purified by silica gel column chromatography (solvent, chloroform:methanol:acetic acid=97:2:1), and the product is crystallized from aqueous ethanol to give the title compound (5.5 g, 60%), m.p. 103°-106° C. (decomp.).

$[\alpha]_D^{20} -196.0°$ (c=1.0, chloroform).

NMR (CDCl$_3$, δ): 2.65 (s, 3H, N—CSSCH$_3$).

Mass (m/e): 306 (M+), 258 (M+—CH$_3$SH).

(ii) In the same manner as described in the above (i), (3R)-1,2,3,4-tetrahydro-β-carboline-3-carboxylic acid (21.62 g), triethylamine (21.25 g), carbon disulfide (8 g), methyl iodide (15.6 g), methanol (42 ml) and water (210 ml) are reacted. The precipitated product is collected by filtration, washed with ether and dried to give triethylamine salt of the title compound (39.3 g, 78%) as colorless needles, m.p. 175°-176° C. (decomp.) (recrystallized from aqueous methanol).

The triethylamine salt obtained above is treated with 10% HCl to give the title compound, which is crystallized from ethanol, m.p. 103°-106° C. (decomp.), $[\alpha]_D^{20} -196.0°$ C. (c=1.0, chloroform).

EXAMPLE 3

(3S)-2-[(Methylthio)thiocarbonyl]-1,2,3,4-tetrahydro-β-carboline-3-carboxylic acid (i) In the same manner as described in Example 2, (i), (3S)-1,2,3,4-tetrahydro-β-carboline-3-carboxylic acid (6.49 g), KOH (3.5 g), carbon disulfide (1.82 ml), methyl iodide (2.5 ml) and 50% ethanol (110 ml) are reacted. The product is treated with dicyclohexylamine to give dicyclohexylamine salt of the title compound (10.69 g, 73%) as colorless needles, m.p. 205° C. (recrystallized from methanol).

The dicyclohexylamine salt obtained above is treated with 10% HCl to give the title compound, which is crystallized from aqueous ethanol, m.p. 103°-105° C. (decomp.).

$[\alpha]_D^{20} +196.4°$ (c=1.0, CHCl$_3$).

NMR (CDCl$_3$, δ): 2.66 (s, 3H, N—CSSCH$_3$).

Mass (m/e): 306 (M+), 258 (M+—CH$_3$SH).

(ii) In the same manner as described in Example 2, (i), (3S)-1,2,3,4-tetrahydro-β-carboline-3-carboxylic acid (21.62 g), NaOH (8.66 g), carbon disulfide (6.4 ml), methyl iodide (7.1 ml), dimethylsulfoxide (150 ml) and water (10 ml) are reacted and treated. The residue thus obtained is purified likewise by silica gel column chromatography (solvent, chloroform:methanol:acetic acid=500:10:1) to give the following two compounds:

(3S)-2,9-Di[(methylthio)thiocarbonyl]-1,2,3,4-tetrahydro-β-carboline-3-carboxylic acid (2.4 g), m.p. 192°-194° C. (recrystallized from chloroform); NMR (CDCl$_3$, δ): 2.70 (s, 3H, N—CSS—CH$_3$), 2.85 (s, 3H, N—CSSCH$_3$); Mass (m/e): 396 (M+)

(3S)-2-[(Methylthio)thiocarbonyl]-1,2,3,4-tetrahydro-β-carboline-3-carboxylic acid (21.4 g, 70%), m.p. 103°-105° C. (decomp.), $[\alpha]_D^{20} +196.4°$ (c=1.0, chloroform)

EXAMPLE 4

(3RS)-2-[(Methylthio)thiocarbonyl]-1,2,3,4-tetrahydro-β-carboline-3-carboxylic acid In the same manner as described in Example 2, (i), (3RS)-1,2,3,4-tetrahydro-β-carboline-3-carboxylic acid (42.25 g), KOH (23.38 g), carbon disulfide (12.1 ml), methyl iodide (16.3 ml) and 50% ethanol (600 ml) are reacted. The product is crystallized from chloroform to give the title compound (50.2 g, 59%), m.p. 111°-113° C., NMR (CDCl$_3$, δ): 2.68 (s, 3H, N—CSSCH$_3$), Mass (m/e): 306 (M+), 258 (M+—CH$_3$SH).

EXAMPLE 5 cl (3RS)-2-[(Methylthio)thiocarbonyl]-1,2,3,4,-tetrahydro-β-carboline-3-carboxylic acid sodium salt (3RS)-2-[(Methylthio)thiocarbonyl]-1,2,3,4-tetrahydro-β-carboline-3-carboxylic acid (1.7 g) is dissolved in a mixture of ethanol (4 ml)-1N NaOH (4 ml) under ice-cooling, and the mixture is distilled under reduced pressure to remove the solvent. The resulting product is lyophilized to give the title compound (1.3 g, quantitatively) as colorless powder. IR $\nu_{max}^{nujol}$(cm$^{-1}$): 1590; NMR (D$_2$O, δ): 2.66 (s, 3H, N—CSSCH$_3$).

EXAMPLE 6

(3RS)-2-[(Ethylthio)thiocarbonyl]-1,2,3,4-tetrahydro-β-carboline-3-carboxylic acid To a mixture of (3RS)-1,2,3,4-tetrahydro-β-carboline-3-carboxylic acid (4.32 g), KOH (96%, 2.34 g) and 50% ethanol (80 ml) is added dropwise carbon disulfide (1.8 ml) at room temperature, and the mixture is stirred at the same temperature for 30 minutes. To the mixture is added dropwise ethyl iodide (4.68 g), and the mixture is further stirred at room temperature for 48 hours and distilled to remove the solvent. To the residue is added water, and the mixture is washed with ether. The aqueous layer is acidified with 10% HCl and extracted with ethyl acetate. The extract is washed with water, dried and then distilled to remove the solvent. The residue is recrystallized from chloroform to give the title compound (4.45 g, 69%) as colorless needles, m.p. 177°–178° C., NMR (CDCl$_3$—DMSO—d$_6$, δ): 1.38 (t, J=7.0 Hz, 3H, N—CSSCH$_2$CH$_3$), 3.34 (q, J=7.0 Hz, 2H, N—CSSCH$_2$CH$_3$), Mass (m/e): 320 (M$^+$), 258 (M$^+$—CH$_3$CH$_2$SH)

EXAMPLE 7

(3RS)-2-[(n-Propylthio)thiocarbonyl]-1,2,3,4-tetrahydro-β-carboline-3-carboxylic acid To a mixture of (3RS)-1,2,3,4-tetrahydro-β-carboline-3-carboxylic acid (4.32 g), dicyclohexylamine (7.3 g) and 50% ethanol (55 ml) is added dropwise carbon disulfide (1.2 ml). The mixture is stirred at room temperature for 30 minutes, and thereto is added dropwise n-propyl iodide (3.4 g). The mixture is further stirred at room temperature for 10 minutes. The reaction mixture is distilled to remove the solvent. The resulting precipitates are collected by filtration and washed with ether to give dicyclohexylamine salt of the title compound. This product is treated with 10% HCl to give the title compound (4.6 g, 69%) as colorless needles, m.p. 180° C. (decomp.) (recrystallized from ethanol).

NMR (CDCl$_3$—DMSO—d$_6$, δ): 1.04 (t, J=7.0 Hz, 3H, N—CSSCH$_2$CH$_2$CH$_3$).

Mass (m/e): 258 (M$^+$—CH$_3$CH$_2$CH$_2$SH).

EXAMPLE 8

(3RS)-2-[(Isopropylthio)thiocarbonyl]-1,2,3,4-tetrahydro-β-carboline-3-carboxylic acid In the same manner as described in Example 6, (3RS)-1,2,3,4-tetrahydro-β-carboline-3-carboxylic acid (3.24 g), KOH (96%, 1.75 g), carbon disulfide (0.91 ml) and isopropyl iodide (1.8 ml) are reacted and treated. The product is crystallized from chloroform to give the title compound (1.59 g) as colorless needles, m.p. 188°–190° C.

NMR (CDCl$_3$—DMSO—d$_6$, δ): 1.45 (d, 6H, J=6 Hz, N—CSSCH(CH$_3$)$_2$).

Mass (m/e): 258 (M$^+$—HSCH(CH$_3$)$_2$).

EXAMPLE 9

(3RS)-2-[(n-Butylthio)thiocarbonyl]-1,2,3,4-tetrahydro-β-carboline-3-carboxylic acid In the same manner as described in Example 6, (3RS)-1,2,3,4-tetrahydro-β-carboline-3-carboxylic acid (3.24 g), KOH (96%, 1.75 g), 50% ethanol (65 ml), carbon disulfide (0.91 ml) and n-butyl iodide (3.3 g) are reacted and treated. The product is crystallized from chloroform to give the title compound (1.9 g) as pale yellow crystals, m.p. 163°–164° C.

NMR (DMSO—d$_6$, δ): 0.91 (m, 3H, N—CSS(CH$_2$)$_3$—CH$_3$).

Mass (m/e): 348 (M$^+$), 258 (M$^+$—HS(CH$_2$)$_3$—CH$_3$).

EXAMPLE 10

(3RS)-2-[(Cyclohexylthio)thiocarbonyl]-1,2,3,4-tetrahydro-β-carboline-3-carboxylic acid In the same manner as described in Example 6, (3RS)-1,2,3,4-tetrahydro-β-carboline-3-carboxylic acid (4.32 g), NaOH (1.8 g), dimethylsulfoxide (25 ml), water (2 ml), carbon disulfide (1.45 ml) and cyclohexyl bromide (3.9 g) are reacted and treated. The product is crystallized from chloroform-n-hexane to give the title compound (4.5 g, 61%), m.p. 150.5°–151° C.

Mass (m/e): 258

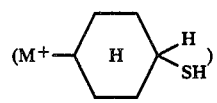

EXAMPLE 11

(3RS)-2-[(n-Decylthio)thiocarbonyl]-1,2,3,4-tetrahydro-β-carboline-3-carboxylic acid In the same manner as described in Example 6, (3RS)-1,2,3,4-tetrahydro-β-carboline-3-carboxylic acid (4.32 g), NaOH (1.65 g), water (2 ml), dimethylsulfoxide (24 ml), carbon disulfide (1.2 ml) and n-decyl bromide (5.31 g) are reacted and treated. The residue thus obtained is purified by silica gel column chromatography (solvent, chloroform:methanol:acetic acid=98:1:0.5) and then crystallized from n-hexane to give the title compound (4.8 g, 55%), m.p. 152.5°–154° C. (decomp.).

NMR (DMSO—d$_6$, δ): 0.92 (m, 3H, N—CSS(CH$_2$)$_9$—CH$_3$).

Mass (m/e): 432 (M$^+$), 258 (M$^+$—CH$_3$—(CH$_2$)$_9$—SH).

EXAMPLE 12

(3RS)-2-[(Allylthio)thiocarbonyl]-1,2,3,4-tetrahydro-β-carboline-3-carboxylic acid In the same manner as described in Example 6, (3RS)-1,2,3,4-tetrahydro-β-carboline-3-carboxylic acid (3.24 g), KOH (1.75 g), 50% ethanol (60 ml), carbon disulfide (1.8 ml) and allyl chloride (2.3 g) are reacted and treated. The product is crystallized from chloroform to give the title compound (3.0 g, 59%), m.p. 161°–162° C.

Mass (m/e): 258 (M$^+$—CH$_2$=CHCH$_2$SH)

EXAMPLE 13

(3RS)-2-[(Methylthiomethylthio)thiocarbonyl]-1,2,3,4-tetrahydro-β-carboline-3-carboxylic acid In the same manner as described in Example 6, (3RS)-1,2,3,4-tetrahydro-β-carboline-3-carboxylic acid (3.24 g), KOH (1.75 g), 50% ethanol (70 ml), carbon disulfide (0.91 ml) and methylthiomethyl chloride (1.74 g) are reacted and treated. The product thus obtained is purified by silica gel column chromatography (solvent, chloroform:methanol:acetic acid=97:2:1) to give the title compound (2.61 g) as a pale yellow powder.

NMR (CDCl$_3$, δ): 2.19 (s, 3H, N—CSSCH$_2$SCH$_3$).

Mass (m/e): 258 (M$^+$—HSCH$_2$SCH$_3$).

EXAMPLE 14

(3RS)-2-[(2-(Dimethylamino)ethylthio)thiocarbonyl]-1,2,3,4-tetrahydro-β-carboline-3-carboxylic acid In the same manner as described in Example 6, (3RS)-1,2,3,4-tetrahydro-β-carboline-3-carboxylic acid (2.16 g), 10N NaOH (2 ml), dimethylsulfoxide (6 ml), carbon disulfide (912 mg) and 2-(dimethylamino)ethyl chloride hydrochloride (1.73 g) are reacted. The precipitates are collected by filtration, washed with water and ethanol, and then dried to give the title compound (3.11 g, quantitatively) as yellow powder.

NMR (DMSO—$d_6$—$CF_3COOH$, δ): 2.90 (s, 6H, N—$CSSCH_2CH_2N(CH_3)_2$).

EXAMPLE 15

(3RS)-2-[(Ethoxycarbonylmethylthio)thiocarbonyl]-1,2,3,4-tetrahydro-β-carboline-3-carboxylic acid In the same manner as described in Example 6, (3RS)-1,2,3,4-tetrahydro-β-carboline-3-carboxylic acid (2.16 g), 10N NaOH (2 ml), dimethylsulfoxide (6 ml), carbon disulfide (912 mg) and ethyl bromoacetate (2.0 g) are reacted. The product is recrystallized from ethanol to give the title compound (1.41 g, 65%) as colorless needles, m.p. 190°–192° C.

NMR ($CDCl_3$—DMSO—$d_6$, δ): 1.30 (t, 3H, J=7.2 Hz, N—$CSSCH_2COOCH_2CH_3$).

Mass (m/e): 378 (M+), 2.58 (M+—$HSCH_2COOCH_2CH_3$).

EXAMPLE 16

(3R)-2-[(Benzylthio)thiocarbonyl]-1,2,3,4-tetrahydro-β-carboline-3-carboxylic acid To a mixture of (3R)-1,2,3,4-tetrahydro-β-carboline-3-carboxylic acid (5.4 g), 2N NaOH (25 ml) and 50% ethanol (70 ml) is added dropwise carbon disulfide (1.5 ml) at room temperature. The mixture is stirred at room temperature for 30 minutes, and thereto is added dropwise benzyl bromide (3.5 ml), and the mixture is further stirred at the same temperature for 3 hours and then distilled to remove the solvent. To the residue is added water, and the mixture is extracted with ether. The aqueous layer is acidified with 10% HCl, extracted with ethyl acetate. The extract is washed with water, dried and distilled to remove the solvent. The residue is purified by silica gel column chromatography (solvent, chloroform:methanol=20:1) to give the title compound (4.5 g) as pale yellow powder.

$[α]_D^{20}$ −103.4° (c=2.0, $CHCl_3$).

NMR ($CDCl_3$, δ): 4.56 (s, 2H, N—$CSSCH_2C_6H_5$).

Mass (m/e): 258 (M+—$C_6H_5CH_2SH$).

EXAMPLE 17

(3S)-2-[(Benzylthio)thiocarbonyl]-1,2,3,4-tetrahydro-β-carboline-3-carboxylic acid In the same manner as described in Example 16, (3S)-1,2,3,4-tetrahydro-β-carboline-3-carboxylic acid (21.6 g), $K_2CO_3$ (13.8 g), water (550 ml), ethanol (550 ml), carbon disulfide (6 ml) and benzyl bromide (14 ml) are reacted and treated. The residue is purified by silica gel column chromatography (solvent, chloroform:methanol=10:1) to give the title compound (20 g, 52.3%) as powder.

$[α]_D^{20}$ +100.7° (c=2.0, $CHCl_3$).

NMR ($CDCl_3$, δ): 4.57 (s, 2H, N—$CSSCH_2C_6H_5$).

Mass (m/e): 258 (M+—$C_6H_5CH_2SH$).

EXAMPLE 18

(3RS)-2-[(Benzylthio)thiocarbonyl]-1,2,3,4-tetrahydro-β-carboline-3-carboxylic acid To a mixture of (3RS)-1,2,3,4-tetrahydro-β-carboline-3-carboxylic acid (5.4 g), 2N NaOH (25 ml) and 50% ethanol (70 ml) is added dropwise carbon disulfide (1.5 ml) at room temperature. The mixture is stirred at room temperature for 30 minutes, and thereto is added dropwise benzyl bromide (3.5 ml), and the mixture is further stirred at the same temperature for 3 hours and then distilled to remove the solvent. To the residue is added water, and the mixture is extracted with ether. The aqueous layer is acidicied with 10% HCl, and extracted with ethyl acetate. The extract is washed with water, dried and distilled to remove the solvent. The residue is purified by silica gel column chromatography (solvent, chloroform:methanol=20:1) to give the title compound (4.8 g, 50%) as pale yellow powder.

NMR ($CDCl_3$, δ): 4.56 (s, 2H, N—$CSSCH_2C_6H_5$).

Mass (m/e): 258 (M+—$C_6H_5CH_2SH$).

EXAMPLE 19

(3R)-2-[(4-Chlorobenzylthio)thiocarbonyl]-1,2,3,4-tetrahydro-β-carboline-3-carboxylic acid In the same manner as described in Example 16, (3R)-1,2,3,4-tetrahydro-β-carboline-3-carboxylic acid (5.4 g), 2N NaOH (25 ml), 50% ethanol (70 ml), carbon disulfide (1.45 ml) and 4-chlorobenzyl chloride (5.65 g) are reacted and treated. The residue is purified by silica gel column chromatography (solvent, chloroform:methanol:acetic acid=97:2:1) to give the title compound (5.86 g, 57%) as pale yellow powder.

$[α]_D^{20}$ −129.5° (c=2.0, methanol).

NMR ($CDCl_3$, δ): 4.52 (s, 2H, N—$CSSCH_2C_6H_4$—p—Cl).

Mass (m/e): 2.58 (M+—p—Cl—$C_6H_4CH_2SH$).

EXAMPLE 20

(3S)-2-[(4-Chlorobenzylthio)thiocarbonyl]-1,2,3,4-tetrahydro-β-carboline-3-carboxylic acid In the same manner as described in Example 16, (3S)-1,2,3,4-tetrahydro-β-carboline-3-carboxylic acid (1.08 g), 2N NaOH (5 ml), 50% ethanol (15 ml), carbon disulfide (0.3 ml) and 4-chlorobenzyl chloride (1.13 g) are reacted and treated. The product is crystallized from n-hexane to give the title compound (1.44 g, 69%), m.p. 139°–141° C. (decomp.).

$[α]_D^{20}$ +134.8° (c=2.0, methanol).

NMR ($CDCl_3$, δ): 4.52 (s, 2H, N—$CSSCH_2C_6H_4$—p—Cl).

Mass (m/e): 258 (M+—p—Cl—$C_6H_4CH_2SH$).

EXAMPLE 21

(3RS)-2-[(4-Chlorobenzylthio)thiocarbonyl]-1,2,3,4-tetrahydro-β-carboline-3-carboxylic acid In the same manner as described in Example 16, (3RS)-1,2,3,4-tetrahydro-β-carboline-3-carboxylic acid (1.08 g), 2N NaOH (5 ml), 50% ethanol (15 ml), carbon disulfide (0.3 ml) and 4-chlorobenzyl chloride (1.13 g) are reacted and treated. The product is purified by silica gel column chromatography (solvent, chloroform:methanol:acetic acid=97:2:1) to give the title compound (1.36 g, 65%), as pale yellow powder.

NMR ($CDCl_3$, δ): 4.52 (s, 2H, N—$CSSCH_2C_6H_4$—p—Cl).

Mass (m/e): 258 (M+—p—Cl—C₆H₄CH₂SH).

EXAMPLE 22

(3R)-2-[(3,4-Dichlorobenzylthio)thiocarbonyl]-1,2,3,4-tetrahydro-β-carboline-3-carboxylic acid In the same manner as described in Example 16, (3R)-1,2,3,4-tetrahydro-β-carboline-3-carboxylic acid (3.24 g), KOH (1.75 g), 70% ethanol (45 ml), carbon disulfide (0.88 ml) and 3,4-dichlorobenzyl chloride (3.52 g) are reacted and treated. The product is purified by silica gel column chromatography (solvent, chloroform:methanol:acetic acid=97:2:1) to give the title compound (3.37 g, 51%), as pale yellow powder.

[α]$_D^{20}$ −129.2° (c=1.0, methanol).

NMR (CDCl₃—DMSO—d₆, δ): 4.54 (s, 2H,

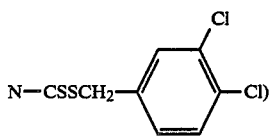

Mass (m/e): 2.58

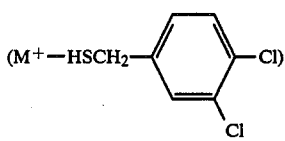

EXAMPLE 23

(3S)-2-[(3,4-Dichlorobenzylthio)thiocarbonyl]-1,2,3,4-tetrahydro-β-carboline-3-carboxylic acid In the same manner as described in Example 16, (3S)-1,2,3,4-tetrahydro-β-carboline-3-carboxylic acid (3.24 g), KOH (1.75 g), 70% ethanol (45 ml), carbon disulfide (0.88 ml) and 3,4-dichlorobenzyl chloride (3.52 g) are reacted and treated. The product is purified by silica gel column chromatography (solvent, chloroform:methanol:acetic acid=97:2:1) to give the title compound (3.63 g, 54%), as pale yellow powder.

[α]$_D^{20}$ +131.4° (c=1.0, methanol).

NMR (CDCl₃—DMSO—d₆, δ): 4.54 (s, 2H,

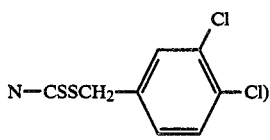

Mass (m/e): 258

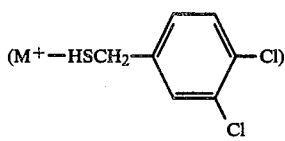

EXAMPLE 24

(3R)-2-[(4-Benzyloxycarbonylamino)benzylthio)thiocarbonyl]-1,2,3,4-tetrahydro-β-carboline-3-carboxylic acid In the same manner as described in Example 16, (3R)-1,2,3,4-tetrahydro-β-carboline-3-carboxylic acid (0.54 g), KOH (0.29 g), 70% ethanol (17 ml), carbon disulfide (0.15 ml) and 4-(benzyloxycarboxylamino)benzyl chloride (0.76 g) are reacted and treated. The product is purified by silica gel column chromatography (solvent, chloroform:methanol:acetic acid=97:2:1) to give the title compound (0.51 g), as pale yellow powder.

[α]$_D^{20}$ −97.0° (c=1.0, methanol).

NMR (CDCl₃, δ): 4.47 (s, 2H,

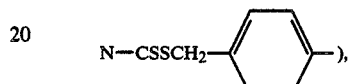

5.11 (s, 2H,

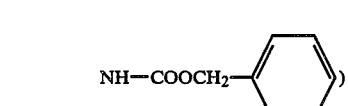

Mass (m/e): 258

EXAMPLE 25

(3R)-2-[(4-Formylamino)benzylthio)thiocarbonyl]-1,2,3,4-tetrahydro-β-carboline-3-carboxylic acid In the same manner as described in Example 16, (3R)-1,2,3,4-tetrahydro-β-carboline-3-carboxylic acid (3.24 g), KOH (1.75 g), carbon disulfide (0.91 ml), dimethylsulfoxide (15 ml), water (7 ml) and 4-(formylamino)benzyl chloride (2.54 g) are reacted and treated. The product is purified by silica gel column chromatography (solvent, chloroform:methanol:acetic acid=94:5:1) to give the title compound (2.58 g), as pale yellow powder.

[α]$_D^{20}$ −132.6° (c=1.0, methanol).

NMR (CDCl₃—DMSO—d₆, δ): 4.57 (s, 2H,

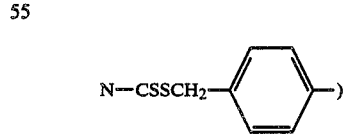

Mass (m/e): 258

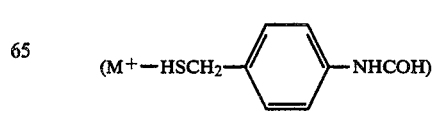

EXAMPLE 26

(3R)-2-[(4-aminobenzylthio)thiocarbonyl]-1,2,3,4-tetrahydro-β-carboline-3-carboxylic acid (3R)-2-[(4-(Formylamino)benzylthio)thiocarbonyl]-1,2,3,4-tetrahydro-β-carboline-3-carboxylic acid (1.46 g) is dissolved in ethanol (34 ml) and thereto is added thioglycolic acid (0.04 ml) and is further added dropwise 6N HCl (34 ml). The mixture is stirred under argon stream for 2.5 hours and then distilled under reduced pressure to remove the solvent. The residue is purified by silica gel column chromatography (solvent, chloroform:methanol:acetic acid=94:5:1-20:10:1) to give the title compound (0.52 g), as pale yellow powder.

$[\alpha]_D^{20}$ −118.0° (c=0.5, ethanol).

NMR (CDCl₃—DMSO—d₆, δ): 4.45 (s, 2H,

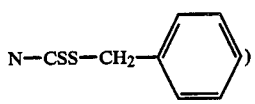

Mass (m/e): 258

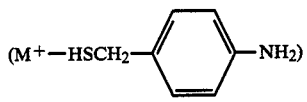

EXAMPLE 27

(3RS)-2-[(4-Methoxybenzylthio)thiocarbonyl]-1,2,3,4-tetrahydro-B-carboline-3-carboxylic acid In the same manner as described in Example 16, (3RS)-1,2,3,4-tetrahydro-β-carboline-3-carboxylic acid (4.32 g), 10N NaOH (4 ml), carbon disulfide (1.4 ml), dimethylsulfoxide (20 ml) and 4-methoxybenzyl bromide (4.02 g) are reacted and treated. The product is crystallized from isopropyl ether to give the title compound (6.50 g, 79%) as colorless needles, m.p. 195°-196° C.

NMR (CDCl₃—DMSO—d₆, δ): 3.81 (s, 3H,

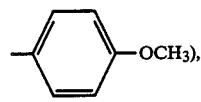

4.59 (s, 2H,

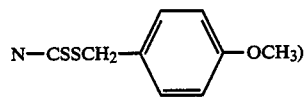

Mass (m/e): 412 (M+), 258

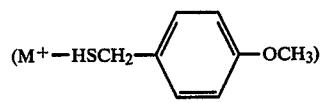

EXAMPLE 28

(3RS)-2-[(4-Nitrobenzylthio)thiocarbonyl]-1,2,3,4-tetrahydro-β-carboline-3-carboxylic acid In the same manner as described in Example 16, (3RS)-1,2,3,4-tetrahydro-β-carboline-3-carboxylic acid (4.22 g), 10N NaOH (3.9 ml), carbon disulfide (1.4 ml), dimethylsulfoxide (12 ml) and 4-nitrobenzyl bromide (4.63 g) are reacted and treated. The product is crystallized from ethanol to give the title compound (4.7 g, 54%) as yellow crystals, m.p. 194°-195° C.

NMR (DMSO—d₆, δ): 4.81 (s, 2H,

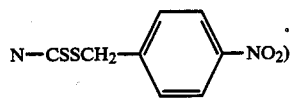

Mass (m/e): 258

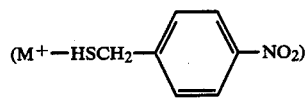

EXAMPLE 29

(3RS)-2-[(4-Methylbenzylthio)thiocarbonyl]-1,2,3,4-tetrahydro-β-carboline-3-carboxylic acid In the same manner as described in Example 16, (3RS)-1,2,3,4-tetrahydro-β-carboline-3-carboxylic acid (4.22 g), 10N NaOH (3.9 ml), carbon disulfide (1.4 ml), dimethylsulfoxide (12 ml) and 4-methylbenzyl chloride (3.3 g) are reacted and treated. The product is crystallized from ethanol to give the title compound (3.13 g), m.p. 188°-190° C.

NMR (CDCl₃—DMSO—d₆, δ): 2.30 (s, 3H,

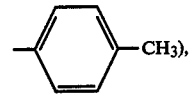

4.56 (s, 2H,

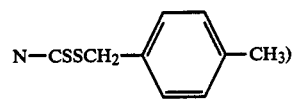

Mass (m/e): 258

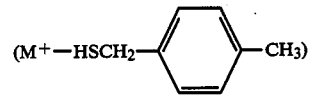

EXAMPLE 30

(3RS)-2-[(4-Carboxybenzylthio)thiocarbonyl]-1,2,3,4-tetrahydro-β-carboline-3-carboxylic acid In the same manner as described in Example 16, (3RS)-1,2,3,4-tetrahydro-β-carboline-3-carboxylic acid (1.08 g), 10N NaOH (1.5 ml), carbon disulfide (456 mg), dimethylsulfoxide and 4-bromomethylbenzoic acid (1.29 g) are reacted and treated. The product is crystallized from chloroform to give the title compound (1.23 g, 53%), m.p. 152°–153° C. (decomp.).

NMR (CDCl₃—DMSO—d₆, δ): 4.71 (s, 2H,

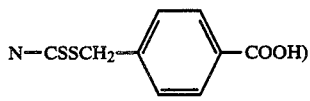

Mass (m/e): 258

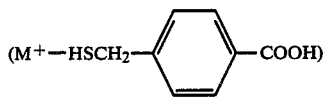

EXAMPLE 31

(3R)-2-[(3-Trifluoromethyl)benzylthio)thiocarbonyl]-1,2,3,4-tetrahydro-β-carboline-3-carboxylic acid In the same manner as described in Example 16, (3R)-1,2,3,4-tetrahydro-β-carboline-3-carboxylic acid (0.92 g), 2N NaOH (4.5 ml), carbon disulfide (0.27 ml), 50% ethanol (15 ml) and 3-(trifluoromethyl)benzyl chloride (0.73 ml) are reacted and treated. The product is purified by silica gel column chromatography to give the title compound (0.73 g) as powder.

[α]$_D^{20}$ −121.0° (c=0.2, methanol).

NMR (CDCl₃—DMSO—d₆, δ): 4.69 (s, 2H, N—CSSCH₂—C₆H₄—m—CF₃).

Mass (m/e): 258 (M⁺—HSCH₂C₆H₄—m—CF₃).

EXAMPLE 32

(3R)-2-[(2-Thenylthio)thiocarbonyl]-1,2,3,4-tetrahydro-β-carboline-3-carboxylic acid and
(3R)-2,9-di[(2-thenylthio)thiocarbonyl]-1,2,3,4-tetrahydro-β-carboline-3-carboxylic acid (3R)-1,2,3,4-Tetrahydro-β-carboline-3-carboxylic acid (8.43 g) is dissolved in dimethylsulfoxide (25 ml) and thereto is added 20N NaOH (4.3 ml) and is further added dropwise carbon disulfide (2.83 ml) at 20° C. The mixture is stirred at the same temperature for 30 minutes, and to the mixture is added dropwise 2-thenyl chloride (6.2 g). The mixture is stirred at room temperature for one hour. The reaction mixture is poured to water and is extracted with ether-n-hexane (1:4). The aqueous layer is acidified with 10% HCl and extracted with ethyl acetate. The extract is washed with water, dried and then distilled to remove the solvent. The residue is purified by silica gel column chromatography (solvent, chloroform:methanol:acetic acid=98:1:1) to give the following two compounds.

Fraction 1:
(3R)-2,9-Di[(2-thenylthio)thiocarbonyl]-1,2,3,4-tetrahydro-β-carboline-3-carboxylic acid (280 mg) as pale yellow powder,

[α]$_D^{20}$ −218.4° (c=1.0, chloroform).

NMR (CDCl₃, δ): 4.85 (s, 4H,

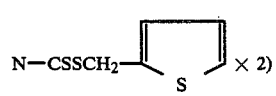

Fraction 2:
(3R)-2-[(2-Thenylthio)thiocarbonyl]-1,2,3,4-tetrahydro-β-carboline-3-carboxylic acid (9.8 g, 65%) as pale yellow powder,

[α]$_D^{20}$ −134.8° (c=1.0, ethyl acetate).

NMR (CDCl₃, δ): 4.81 (b. s, 2H,

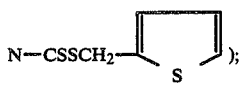

Mass (m/e): 258

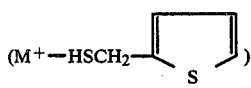

EXAMPLE 33

(3S)-2-[(2-Thenylthio)thiocarbonyl]-1,2,3,4-tetrahydro-β-carboline-3-carboxylic acid In the same manner as descsribed in Example 32, (3S)-1,2,3,4-tetrahydro-β-carboline-3-carboxylic acid (4.33 g), KOH (2.33 g), carbon disulfide (1.22 ml), 50% ethanol (80 ml) and 2-thenyl chloride (3.1 g) are reacted and treated to give the title compound (3.15 g) as pale yellow powder.

[α]$_D^{20}$ +128.2° (c=1.0, ethyl acetate).

NMR (CDCl₃, δ): 4.80 (b. s, 2H,

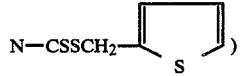

Mass (m/e): 258

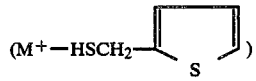

EXAMPLE 34

(3RS)-2-[(2-Thenylthio)thiocarbonyl]-1,2,3,4-tetrahydro-β-carboline-3-carboxylic acid In the same manner as descsribed in Example 32, (3RS)-1,2,3,4-tetrahydro-β-carboline-3-carboxylic acid (4.32 g), 20N NaOH (2.2 ml), carbon disulfide (1.45 ml), dimethylsulfoxide (13 ml) and 2-thenyl chloride (3.18 g) are reacted and treated. The product is crystallized from ethanol to give the title compound (4.1 g) as pale yellow crystals, m.p. 172° C. (decomp.).

NMR (CDCl₃, δ): 4.84 (s, 2H,

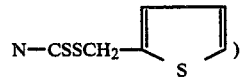

Mass (m/e): 258

($M^+$—HSCH$_2$— 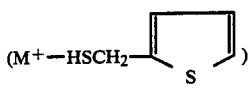)

EXAMPLE 35

(3R)-2-[(Furfurylthio)thiocarbonyl]-1,2,3,4-tetrahydro-β-carboline-3-carboxylic acid In the same manner as descsribed in Example 32, (3R)-1,2,3,4-tetrahydro-β-carboline-3-carboxylic acid (8.65 g), KOH (4.67 g), carbon disulfide (2.43 ml), 75% ethanol (120 ml) and furfuryl chloride which is prepared from furfuryl alcohol (9.24 g), thionyl chloride (12.34 g) and pyridine (8.94 g) are reacted and treated to give the title compound (2.31 g) as pale yellow powder.

$[\alpha]_D^{20}$ −151.2° (c=1.0, methanol).

NMR (CDCl$_3$, δ): 4.60 (b. s, 2H,

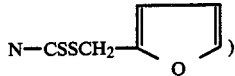
N—CSSCH$_2$— )

Mass (m/e): 372 ($M^+$), 258

($M^+$—HSCH$_2$— 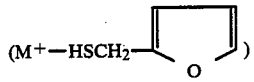)

EXAMPLE 36

(3RS)-2-[(2-Pyridylmethylthio)thiocarbonyl]-1,2,3,4-tetrahydro-β-carboline-3-carboxylic acid In the same manner as descsribed in Example 32, (3RS)-1,2,3,4-tetrahydro-β-carboline-3-carboxylic acid (3.24 g), KOH (1.75 g), carbon disulfide (0.91 ml), 50% ethanol (70 ml) and 2-pyridylmethyl chloride hydrochloride (2.95 g) are reacted and treated to give the title compound (2.07 g) as pale yellow powder.

NMR (DMSO—d$_6$, δ): 4.76 (s, 2H,

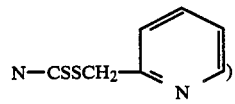
N—CSSCH$_2$— )

Mass (m/e): 258

($M^+$—HSCH$_2$— 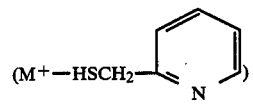)

EXAMPLE 37

(3R)-2-[(1-Naphthylmethylthio)thiocarbonyl]-1,2,3,4-tetrahydro-β-carboline-3-carboxylic acid In the same manner as descsribed in Example 32, (3R)-1,2,3,4-tetrahydro-β-carboline-3-carboxylic acid (3.24 g), KOH (1.75 g), carbon disulfide (0.91 ml), 50% ethanol (70 ml) and 1-naphthylmethyl chloride (3.14 g) are reacted and treated to give the title compound (2.84 g) as pale yellow powder.

$[\alpha]_D^{20}$ −90.4° (c=1.0, chloroform).

NMR (CDCl$_3$, δ): 4.98 (s, 2H, N—CSSCH$_2$—C$_{10}$H$_7$).

Mass (m/e): 258 ($M^+$—HSCH$_2$—C$_{10}$H$_7$).

EXAMPLE 38

(3RS)-2-[(Phenethylthio)thiocarbonyl]-1,2,3,4-tetrahydro-β-carboline-3-carboxylic acid In the same manner as descsribed in Example 32, (3RS)-1,2,3,4-tetrahydro-β-carboline-3-carboxylic acid (3.24 g), KOH (1.75 g), carbon disulfide (0.91 ml), dimethylsulfoxide (20 ml), water (5 ml) and phenethyl bromide (3.33 g) are reacted and treated. The product is crystallized from chloroform to give the title compound (2.77 g), m.p. 89°–90° C.

NMR (CDCl$_3$—DMSO—d$_6$, δ): 6.90–7.65 (m, 9H, Aromatic H).

Mass (m/e): 396 ($M^+$), 258 ($M^+$—HSCH$_2$CH$_2$C$_6$H$_5$).

EXAMPLE 39

(3RS)-2-[(Cinnamylthio)thiocarbonyl]-1,2,3,4-tetrahydro-β-carboline-3-carboxylic acid In the same manner as descsribed in Example 32, (3RS)-1,2,3,4-tetrahydro-β-carboline-3-carboxylic acid (2.16 g), 10N NaOH (2 ml), carbon disulfide (912 mg), dimethylsulfoxide (6 ml) and cinnamyl bromide (2.364 g) are reacted and treated. The product is crystallized from ethanol to give the title compound (1.34 g), m.p. 200°–202° C.

NMR (CDCl$_3$—DMSO—d$_6$, δ): 6.92–7.50 (m, 9H).

Mass (m/e): 258

($M^+$—HSCH$_2$—CH=CH— 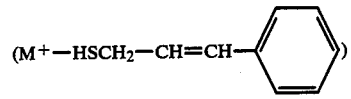)

EXAMPLE 40

(3RS)-2-[(Phenacylthio)thiocarbonyl]-1,2,3,4-tetrahydro-β-carboline-3-carboxylic acid To a mixture of (3RS)-1,2,3,4-tetrahydro-β-carboline-3-carboxylic acid (4.32 g), triethylamine (5.8 ml), ethanol (15 ml) and water (25 ml) is added dropwise carbon disulfide (1.26 ml). The mixture is stirred at room temperature for 30 minutes, and to the mixture is added phenacyl bromide (4.18 g), and the mixture is stirred for 20 minutes. The precipitates are collected by filtration, washed with water and ether to give triethylamine salt of the title compound (9.0 g, 88%), m.p. 146°–147° C. (decomp.) (recrystallized from methanol).

The above triethylamine salt is treated with 10% HCl and recrystallized from ethanol—water to give the title compound, m.p. 116° C.

NMR (CDCl$_3$—DMSO—d$_6$, δ): 5.62 (s, 2H, N—CSSCH$_2$COC$_6$H$_5$).

Mass (m/e): 258 ($M^+$—HSCH$_2$COC$_6$H$_5$).

EXAMPLE 41

(3RS)-2-[(Phenylthio)thiocarbonyl]-1,2,3,4-tetrahydro-β-carboline-3-carboxylic acid (3RS)-1,2,3,4-Tetrahydro-β-carboline-3-carboxylic acid (3.24 g) is dissolved in dimethylsulfoxide (9 ml) and thereto is added 10N NaOH (33 ml) and further added carbon disulfide (0.91 ml) at room temperature. The mixture is stirred at room temperature for one hour, and to the mixture is added benzenediazonium chloride which is prepared from aniline (1.49 g), NaNO₂ (1.15 g), conc. HCl (4.8 ml) and water (18.5 ml), and the mixture is stirred at 10° C. for one hour. The reaction mixture is treated in the same manner as described in Example 32. The product is crystallized from ethanol to give the title compound (676 mg) as pale yellow prisms, m.p. 167°–168° C. (decomp.).

NMR (CDCl₃, δ): 7.0–7.60 (m, 9H, aromatic H).

EXAMPLE 42

(1S,3S)-1-Methyl-2-[(methylthio)thiocarbonyl]-1,2,3,4-tetrahydro-β-carboline-3-carboxylic acid To a mixture of (1S,3S)-1-methyl-1,2,3,4-tetrahydro-β-carboline-3-carboxylic acid (2.30 g), 10N NaOH (2 ml) and dimethylsulfoxide (6 ml) is added dropwise carbon disulfide (912 mg) and further added dropwise methyl iodide (1.7 g) at 0° C. The mixture is stirred at room temperature for one hour, and to the mixture is added water, and then extracted with ethyl acetate. The aqueous layer is acidified with 10% HCl and extracted with ethyl acetate. The extract is dried and distilled to remove the solvent. The residue is crystallized from chloroform to give the title compound (1.59 g, 50%) as colorless needles, m.p. 134°–137° C. (decomp.).

$[\alpha]_D^{20} +234.6°$ (c=1.0, methanol).

NMR (CDCl₃, δ): 1.70 (d, J=7.2 Hz, 3H, C₁—CH₃), 2.75 (s, 3H, N—CSSCH₃).

Mass (m/e): 320 (M⁺), 272 (M⁺—CH₃SH).

EXAMPLE 43

(1RS,3SR)-trans-1-Methyl-2-[(methylthio)thiocarbonyl]-1,2,3,4-tetrahydro-β-carboline-3-carboxylic acid (1RS,3SR)-trans-1-Methyl-1,2,3,4-tetrahydro-β-carboline-3-carboxylic acid (1.15 g) is dissolved in methanol (30 ml)—water (3 ml) and thereto are added triethylamine (1.9 g) and carbon disulfide (912 mg). The mixture is stirred at room temperature for 20 minutes, and to the mixture is added methyl iodide (1.7 g) and the mixture is stirred at room temperature for 2 hours and then distilled under reduced pressure to remove the solvent. To the residue is added water, and the aqueous solution is acidified with 10% HCl and extracted with ethyl acetate. The extract is washed with water, dried and distilled to remove the solvent. The residue is recrystallized from aqueous ethanol to give the title compound (1.13 g, 70.6%) as colorless needles, m.p. 173°–176° C.

NMR (CDCl₃, δ): 1.65 (d, J'6.5 Hz, 3H, C₁—CH₃), 2.64 (s, 3H, N—CSSCH₃).

Mass (m/e): 272 (M⁺—CH₃SH).

EXAMPLE 44

(1RS,3RS)-cis-1-Ethyl-2-[(methylthio)thiocarbonyl]-1,2,3,4-tetrahydro-β-carboline-3-carboxylic acid In the same manner as described in Example 43, (1RS,3RS)-cis-1-ethyl-1,2,3,4-tetrahydro-β-carboline-3-carboxylic acid (1.22 g), triethylamine (1.21 g), carbon disulfide (456 mg), methyl iodide (852 mg), methanol (30 ml) and water (3 ml) are reacted and treated. The product is recrystallized from aqueous ethanol to give the title compound (880 mg, 52.7%) as colorless prisms, m.p. 198°–200° C.

NMR (CDCl₃—DMSO—d₆, δ): 2.67 (s, 3H, N—CSSCH₃).

Mass (m/e): 334 (M⁺), 286 (M⁺—CH₃SH).

EXAMPLE 45

(1RS,3SR)-trans-1-Ethyl-2-[(methylthio)thiocarbonyl]-1,2,3,4-tetrahydro-β-carboline-3-carboxylic acid In the same manner as described in Example 43, (1RS,3SR)-trans-1-ethyl-1,2,3,4-tetrahydro-β-carboline-3-carboxylic acid (733 mg), triethylamine (707 mg), carbon disulfide (305 mg), methyl iodide (568 mg), methanol (20 ml) and water (2 ml) are reacted and treated. The product is recrystallized from aqueous ethanol to give the title compound (700 mg, 70%) as colorless prisms, m.p. 155°–157° C.

MNR (CDCl₃, δ): 2.60 (s, 3H, N—CSSCH₃).

Mass (m/e): 286 (M⁺—CH₃SH).

EXAMPLE 46

(1RS,3RS)-cis-1-n-Butyl-2-[(methylthio)thiocarbonyl]-1,2,3,4-tetrahydro-β-carboline-3-carboxylic acid In the same manner as described in Example 43, (1RS,3RS)-cis-1-n-butyl-1,2,3,4-tetrahydro-β-carbonline-3-carboxylic acid (1.0 g), triethylamine (0.85 g), carbon disulfide (0.32 g), methyl iodide (0.6 g), methanol (20 ml) and water (10 ml) are reacted and treated. The product is recrystallized from aqueous ethanol to give the title compound (0.95 g, 71%), m.p. 100°–105° C. (decomp.).

NMR (CDCl₃, δ): 2.72 (s, 3H, N—CSSCH₃).

Mass (m/e): 362 (M⁺), 314 (M⁺—CH₃SH).

EXAMPLE 47

(1RS,3SR)-trans-1-n-Butyl-2-[(methylthio)thiocarbonyl]-1,2,3,4-tetrahydro-β-carboline-3-carboxylic acid In the same manner as described in Example 43, (1RS,3SR)-trans-1-n-butyl-1,2,3,4-tetrahydro-β-carboline-3-carboxylic acid (1.2 g), triethylamine (1.02 g), carbon disulfide (0.39 g), methyl iodide (0.72 g), methanol (14 ml) and water (2 ml) are reacted and treated. The product is recrystallized from aqueous ethanol to give the title compound (1.2 g, 75%), m.p. 99°–102° C. (decomp.).

NMR (CDCl₃, δ): 2.59 (s, 3H, N—CSSCH₃).

Mass (m/e): 314 (M⁺—CH₃SH).

EXAMPLE 48

(1RS,3RS)-cis-1-Hydroxymethyl-2-[(methylthio)-thiocarbonyl]-1,2,3,4-tetrahydro-β-carboline-3-carboxylic acid and methyl (1RS,5RS)-cis-1,2,3,4,5,6,11-hexahydro-4-oxo-1,5-iminooxocino[4,5-b]indole-12-carbodithioate In the same manner as described in Example 43, (1RS,3RS)-cis-1-hydroxymethyl-1,2,3,4-tetrahydro-β-carboline-3-carboxylic acid (54 mg), triethylamine (0.09 ml), carbon disulfide (0.03 ml), methyl iodide (0.03 ml), dimethylsulfoxide (0.5 ml) and water (0.1 ml) are reacted and treated. The product is purified by silica gel column chromatography (solvent, chloroform:methanol=4:1) to give the following two compounds.

Methyl (1RS,5RS)-cis-1,2,4,5,6,11-hexahydro-4-oxo-1,5-iminooxocino[4,5-b]indole-12-carbodithioate (24 mg), m.p. 244°–245° C.

NMR (CDCl₃—DMSO—d₆, δ): 2.67 (s, 3H, N—CSSCH₃).

Mass (m/e): 318 (M⁺).

IR $\nu_{max}^{nujol}$ (cm⁻¹): 1725.

(1RS,3RS)-cis-1-Hydroxymethyl-2-[(methylthio)-thiocarbonyl]-1,2,3,4-tetrahydro-β-carboline-3-carboxylic acid (40 mg, 54%) as white powder.

NMR (CDCl$_3$—DMSO—d$_6$, δ): 2.64 (s, 3H, N—CSSCH$_3$).

EXAMPLE 49

(1RS,3SR)-trans-1-Hydroxymethyl-2-[(methylthio)-thiocarbonyl]-1,2,3,4-tetrahydro-β-carboline-3-carboxylic acid In the same manner as described in Example 43, (1RS,3SR)-trans-1-hydroxymethyl-1,2,3,4-tetrahydro-β-carboline-3-carboxylic acid (1.48 g), triethylamine (1.68 ml), carbon disulfide (0.73 ml), methyl iodide (0.75 ml) and 80% methanol (20 ml) are reacted and treated. The product is crystallized from aqueous ethanol to give the title compound (0.68 g), m.p. 187°–188° C. (decomp.).

NMR (CDCl$_3$–DMSO—d$_6$, δ): 2.66 (s, 3H, N—CSSCH$_3$).

EXAMPLE 50

(3RS)-9-Methyl-2-[(methylthio)thiocarbonyl]-1,2,3,4-tetrahydro-β-carboline-3-carboxylic acid Methyl (3RS)-9-methyl-2-[(methylthio)thiocarbonyl]-1,2,3,4-tetrahydro-β-carboline-3Z-carboxylate (2.84 g) is dissolved in methanol (15 ml)—dimethoxyethane (85 ml) and thereto is added 1N NaOH (10.3 ml). The mixture is stirred at room temperature for 10 hours and distilled under reduced pressure to remove the solvent. The residue is dissolved in water and acidified with 10% HCl and extracted with ethyl acetate. The extract is washed with saturated aqueous sodium chloride solution, dried and distilled to remove the solvent. The residue is recrystallized from ethanol to give the title compound (2.36 g, 86.7%) as colorless needles, m.p. 212°–213° C.

NMR (CDCl$_3$, δ): 2.71 (s, 3H, N—CSSCH$_3$), 3.57 (s, 3H, N—CH$_3$).

Mass (m/e): 320 (M$^+$), 272 (M$^+$—CH$_3$SH).

EXAMPLE 51

(3R)-9-Benzyl-2-[(methylthio)thiocarbonyl]-1,2,3,4-tetrahydro-β-carboline-3-carboxylic acid (3R)-9-Benzyl-1,2,3,4-tetrahydro-β-carboline-3-carboxylic acid (1.225 g) is dissolved in dimethylsulfoxide (20 ml) and thereto are added 10N NaOH (0.8 ml) and carbon disulfide (0.24 ml). The mixture is stirred at room temperature for 10 minutes and thereto is added dropwise methyl iodide (0.29 ml). The mixture is stirred at room temperature for 20 minutes and thereto is added water (100 ml). The mixture is acidified with 10% HCl and extracted with ethyl acetate. The extract is washed with water, dried and distilled to remove the solvent. The residue is purified by silica gel column chromatography (solvent, chloroform:methanol:acetic acid=90:5:1) to give the title compound (0.89 g, 52%) as pale yellow powder.

[α]$_D^{20}$ −199.6° (c'1.0, chloroform).

NMR (CDCl$_3$, δ): 2.65 (s, 3H, N—CSSCH$_3$), 5.17 (s, 2H, N—CH$_2$C$_6$H$_5$).

Mass (m/e): 396 (M$^+$), 348 (M$^+$—CH$_3$SH).

EXAMPLE 52

(3R)-9-Benzyl-2-[(2-thenylthio)thiocarbonyl]-1,2,3,4-tetrahydro-β-carboline-3-carboxylic acid In the same manner as described in Example 51, (3R)-9-benzyl-1,2,3,4-tetrahydro-β-carboline-3-carboxylic acid (1.225 g), 10N NaOH (0.8 ml), carbon disulfide (0.24 ml), dimethylsulfoxide (30 ml) and 2-thenyl chloride (0.66 g) are reacted and treated to give the title compound (0.635 g) as pale yellow powder.

[α]$_D^{20}$ −150.6° (c=1.0, chloroform)

NMR (CDCl$_3$—DMSO—d$_6$, δ): 4.82 (s, 2H,

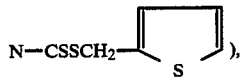), 5.16 (s, 2H, N—CH$_2$C$_6$H$_5$).

Mass (m/e): 478 (M$^+$), 348

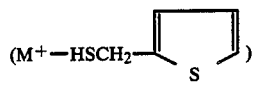)

EXAMPLE 53

Methyl (3RS)-2-[(methylthio)thiocarbonyl]-1,2,3,4-tetrahydro-β-carboline-3-carboxylate Methyl (3RS)-1,2,3,4-tetrahydro-β-carboline-3-carboxylate (2.30 g) is dissolved in methanol (50 ml) and thereto are added triethylamine (1.21 g) and carbon disulfide (920 mg). The mixture is stirred at room temperature for 20 minutes and thereto is added dropwise methyl iodide (1.70 g). The mixture is stirred for 4 hours and distilled under reduced pressure to remove the solvent. The residue is dissolved in ethyl acetate, and the mixture is washed with water, dried and distilled to remove the solvent. The residue is recrystallized from ether-n-hexane to give the title compound (2.10 g, 65.6%) as colorless needles, m.p. 132°–134° C.

NMR (CDCl$_3$, δ): 2.66 (s, 3H, N—CSSCH$_3$), 3.53 (s, 3H, COOCH$_3$).

Mass (m/e): 320 (M$^+$), 229 (M$^+$—CSSCH$_3$).

EXAMPLE 54

Methyl (3S)-2-[(4-chlorobenzylthio)thiocarbonyl]-1,2,3,4-tetrahydro-β-carboline-3-carboxylate (3S)-2-[(4-Chlorobenzylthio)thiocarbonyl]-1,2,3,4-tetrahydro-β-carboline-3-carboxylic acid (2.08 g) is dissolved in methanol (30 ml) and thereto is added dropwise thionyl chloride (0.94 ml) at −20° C. The mixture is stirred at 50°–60° C. for 5 hours and then distilled to remove the solvent. The residue is dissolved in ethyl acetate, and the solution is washed with water, dried, treated with active carbon and distilled to remove the solvent. The residue is recrystallized from ethyl acetate-n-hexane to give the title compound (1.08 g, 50%) as colorless needles, mp 181°–182° C. (decomp.).

[α]$_D^{20}$ +126.6° (c=1.0, chloroform).

NMR (CDCl$_3$, δ): 3.55 (s, 3H, COOCH$_3$), 4.54 (s, 2H, N—CSSCH$_2$C$_6$H$_4$—p—Cl).

Mass (m/e): 430 (M$^+$), 229 (M$^+$—CSSCH$_2$C$_6$H$_4$—p—Cl).

EXAMPLE 55

Methyl (3S)-2-[(2-thienylthio)thiocarbonyl]-1,2,3,4-tetrahydro-β-carboline-3-carboxylate In the same manner as described in Example 53, methyl (3S)-1,2,3,4-tetrahydro-β-carboline-3-carboxylate (5.00 g), triethylamine (2.61 g), carbon disulfide (1.57 ml), methanol (100 ml) and 2-thenyl chloride (3.45 g) are reacted and treated. The product is recrystallized from benzene-n-hexane to give the title compound (6.00 g, 70%) as pale yellow needles, m.p. 150°–152° C.

$[\alpha]_D^{20}+136.8°$ (c=1.0, chloroform).

NMR (CDCl$_3$, δ): 3.61 (s, 3H, COOCH$_3$), 4.86 (s, 2H,

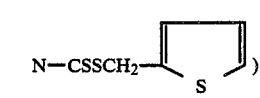

Mass (m/e): 402 (M+).

EXAMPLE 56

Ethyl (3R)-2-[(methylthio)thiocarbonyl]-1,2,3,4-tetrahydro-β-carboline-3-carboxylate In the same manner as described in Example 53, ethyl (3R)-1,2,3,4-tetrahydro-β-carboline-3-carboxylate (224 mg), triethylamine (120 mg), carbon disulfide (0.08 ml), ethanol (25 ml) and methyl iodide (0.08 ml) are reacted and treated. The product is crystallized from ether to give the title compound (140 mg) as colorless prisms, m.p. 139°–141° C.

$[\alpha]_D^{20}-232.4°$ (c=1.0, ethanol).

NMR (CDCl$_3$, δ): 1.08 (t, J=7.2 Hz, 3H, COOCH$_2$CH$_3$), 2.70 (s, 3H, N—CSSCH$_3$)

Mass (m/e): 334 (M+).

EXAMPLE 57

Ethyl (3S)-2-[(methylthio)thiocarbonyl]-1,2,3,4-tetrahydro-β-carboline-3-carboxylate In the same manner as described in Example 53, ethyl (3S)-1,2,3,4-tetrahydro-β-carboline-3-carboxylate (2.50 g), triethylamine (1.34 g), carbon disulfide (0.82 ml), ethanol (60 ml) and methyl iodide (0.84 ml) are reacted and treated. The product is recrystallized from ethyl acetate-n-hexane to give the title compound (2.55 g, 68%) as colorless prisms, m.p. 138°–140° C.

$[\alpha]_D^{20}+232.2°$ (c=1.0, ethanol).

NMR (CDCl$_3$, δ): 1.08 (t, J=7.2 Hz, 3H, COOCH$_2$CH$_3$), 2.70 (s, 3H, N—CSSCH$_3$).

Mass (m/e): 334 (M+).

EXAMPLE 58

Ethyl (3R)-2-[(2-thenylthio)thiocarbonyl]-1,2,3,4-tetrahydro-β-carboline-3-carboxylate In the same manner as described in Example 53, ethyl (3R)-1,2,3,4-tetrahydro-β-carboline-3-carboxylate (2.24 g), triethylamine (1.25 g), carbon disulfide (0.76 ml), ethanol (50 ml) and 2-thenyl chloride (1.65 g) are reacted and treated. The product is recrystallized from ethyl acetate-n-hexane to give the title compound (2.60 g, 63%) as colorless needles, m.p. 205°–207° C.

$[\alpha]_D^{20}-136.0°$ (c=1.0, chloroform)

NMR (CDCl$_3$—DMSO—d$_6$, δ): 1.09 (t, J=7.2 Hz, 3H, COOCH$_2$CH$_3$), 4.85 (s, 2H,

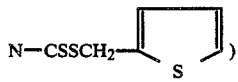

Mass (m/e): 416 (M+).

EXAMPLE 59

Ethyl (3S)-2-[(2-thenylthio)thiocarbonyl]-1,2,3,4-tetrahydro-β-carboline-3-carboxylate In the same manner as described in Example 53, ethyl (3S)-1,2,3,4-tetrahydro-β-carboline-3-carboxylate (2.24 g), triethylamine (1.20 g), carbon disulfide (0.73 ml), ethanol (50 ml) and 2-thenyl chloride (1.59 g) are reacted and treated. The product is recrystallized from ethyl acetate-n-hexane to give the title compound (2.57 g, 62%) as colorless needles, m.p. 206°–207° C.

$[\alpha]_D^{20}+136.0°$ (c=1.0, chloroform).

NMR (CDCl$_3$—DMSO—d$_6$, δ): 1.10 (t, J=7.2 Hz, 3H, COOCH$_2$CH$_3$), 4.85 (s, 2H,

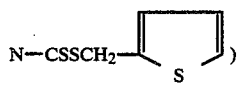

Mass (m/e): 416 (M+).

EXAMPLE 60

Ethyl (3R)-2-[(4-chlorobenzylthio)thiocarbonyl]-1,2,3,4-tetrahydro-β-carboline-3-carboxylate In the same manner as described in Example 53, ethyl (3R)-1,2,3,4-tetrahydro-β-carboline-3-carboxylate (2.00 g), triethylamine (1.07 g), carbon disulfide (0.65 ml), ethanol (60 ml) and 4-chlorobenzyl chloride (1.72 g) are reacted and treated. The product is recrystallized from ethyl acetate-n-hexane to give the title compound (2.75 g, 69%) as pale yellow needles, m.p. 198°–199° C.

$[\alpha]_D^{20}-127.3°$ (c=1.0, chloroform).

NMR (CDCl$_3$, δ): 1.09 (t, J=6.6 Hz, 3H, COOCH$_2$CH$_3$), 4.57 (s, 2H, N—CSSCH$_2$C$_6$H$_4$—p—Cl).

Mass (m/e): 444 (M+).

EXAMPLE 61

Ethyl (3S)-2-[(4-chlorobenzylthio)thiocarbonyl]-1,2,3,4-tetrahydro-β-carboline-3-carboxylate In the same manner as described in Example 53, ethyl (3S)-1,2,3,4-tetrahydro-β-carboline-3-carboxylate (2.00 g), triethylamine (1.07 g), carbon disulfide (0.65 ml), ethanol (60 ml) and 4-chlorobenzyl chloride (1.72 g) are reacted and treated. The product is recrystallized from ethyl acetate-n-hexane to give the title compound (2.59 g, 60%) as pale yellow needles, m.p. 195°–197° C.

$[\alpha]_D^{20}+123.4°$ (c=1.0, chloroform).

NMR (CDCl$_3$, δ): 1.09 (t, J=6.6 Hz, 3H, COOCH$_2$CH$_3$), 4.57 (s, 2H, N—CSSCH$_2$C$_6$H$_4$—p—Cl).

Mass (m/e): 444 (M+).

EXAMPLE 62

Isopropyl (3S)-2-[(4-chlorobenzylthio)thiocarbonyl]-1,2,3,4-tetrahydro-β-carboline-3-carboxylate (3S)-2-[(4-Chlorobenzylthio)thiocarbonyl]-1,2,3,4-tetrahydro-β-carboline-3-carboxylic acid (2.08 g) is suspended in isopropyl alcohol (30 ml) and thereto is added dropwise thionyl chloride (0.47 ml) at −20° C. The mixture is stirred at room temperature for 17 hours and then refluxed at 90° C. for 4 hours. After distilling off the solvent, the residue is dissolved in ethyl acetate. The solution is washed with water, dried and distilled to remove the solvent. The residue is recrystallized from ethyl acetate-n-hexane to give the title compound (477 mg), m.p. 178°–180° C. (decomp.).

$[\alpha]_D^{20} +124.4°$ (c=1.0, chloroform).

NMR (CDCl$_3$, δ): 0.96 (d, 3H, J=6.2 Hz, COOCH(CH$_3$)$_2$), 1.12 (d, 3H, J=6.2 Hz, COOCH(CH$_3$)$_2$), 4.58 (s, 2H, N—CSSCH$_2$C$_6$H$_4$—p—Cl).

Mass (m/e): 458 (M+).

EXAMPLE 63

Methyl (1S,3S)-1-methyl-2-[(methylthio)thiocarbonyl]-1,2,3,4-tetrahydro-β-carboline-3-carboxylate A mixture of (1S,3S)-1-methyl-2-[(methylthio)thiocarbonyl]-1,2,3,4-tetrahydro-β-carboline-3-carboxylic acid (1.28 g), diazomethane [prepared from N-nitrosomethylurea (3.0 g) and 40% NaOH (9 ml)] and ether (100 ml) is allowed to stand under ice-cooling overnight. The resulting precipitates are collected by filtration and dried to give the title compound (1.09 g, 82%), m.p. 229°–230° C.

$[\alpha]_D^{20} +226.9°$ (c=1.0, chloroform)

NMR (CDCl$_3$—DMSO—d$_6$, δ): 1.71 (d, J=6.6 Hz, 3H, C$_1$—CH$_3$), 2.74 (s, 3H, N—CSSCH$_3$), 3.63 (s, 3H, COOCH$_3$).

Mass (m/e): 334 (M+).

EXAMPLE 64

Methyl (3RS)-9-methyl-2-[(methylthio)thiocarbonyl]-1,2,3,4-tetrahydro-β-carboline-3-carboxylate In the same manner as described in Example 53, methyl (3RS)-9-methyl-1,2,3,4-tetrahydro-β-carboline-3-carboxylate hydrochloride (5.61 g), triethylamine (4.86 g), carbon disulfide (1.83 g), methanol (200 ml) and methyl iodide (3.40 g) are reacted and treated. The product is recrystallized from methanol to give the title compound (5.38 g, 80.5%) as colorless needles, m.p. 170°–171° C.

NMR (CDCl$_3$, δ): 2.72 (s, 3H, N—CSSCH$_3$), 3.56 (s, 6H, COOCH$_3$, N—CH$_3$).

Mass (m/e): 334 (M+).

EXAMPLE 65

Methyl (3RS)-9-methyl-2-[(2-thenylthio)thiocarbonyl]-1,2,3,4-tetrahydro-β-carboline-3-carboxylate In the same manner as described in Example 53, methyl (3RS)-9-methyl-1,2,3,4-tetrahydro-β-carboline-3-carboxylate (421 mg), triethylamine (365 mg), carbon disulfide (137 mg), methanol (20 ml) and 2-thenyl chloride (238 mg) are reacted and treated. The product is recrystallized from methanol to give the title compound (360 mg, 57.6%) as colorless prisms, m.p. 139°–140° C.

NMR (CDCl$_3$, δ): 3.57 (s, 6H, N—CH$_3$, COOCH$_3$), 4.84 (s, 2H,

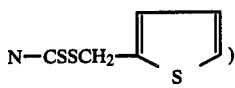

Mass (m/e): 416 (M+).

EXAMPLE 66

Methyl (3R)-2,9-di[(2-thenylthio)thiocarbonyl]-1,2,3,4-tetrahydro-β-carboline-3-carboxylate A mixture of (3R)-2,9-di[(2-thenylthio)thiocarbonyl]-1,2,3,4-tetrahydro-β-carboline-3-carboxylic acid (0.3 g), diazomethane [prepared from N-nitrosomethylurea (1.55 g) and 40% KOH (4.5 ml)] and ether (30 ml) is allowed to stand at 0° C. overnight. Undissolved substances are removed by filtration and the filtrate is concentrated to give the title compound (150 mg, 50%) as pale yellow powder.

NMR (CDCl$_3$, δ): 3.68 (s, 3H, COOCH$_3$), 4.83 (s, 4H,

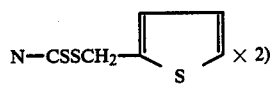

Mass (m/e): 477

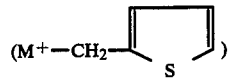

EXAMPLE 67

(3RS)-2-[(Methylthio)thiocarbonyl]-1,2,3,4-tetrahydro-β-carboline-3-carboxamide

In the same manner as described in Example 53, (3RS)-1,2,3,4-tetrahydro-β-carboline-3-carboxamide (0.71 g), triethylamine (0.46 ml), carbon disulfide (0.22 ml), 70% ethanol (20 ml) and methyl iodide (0.22 ml) are reacted and treated. The product is crystallized from ethyl acetate to give the title compound (0.414 g), m.p. 224°–225° C. (decomp.).

NMR (CDCl$_3$—DMSO—d$_6$, δ): 2.75 (s, 3H, N—CSSCH$_3$).

Mass (m/e): 305 (M+).

EXAMPLE 68

(3S)-2-[(4-Chlorobenzylthio)thiocarbonyl]-1,2,3,4-tetrahydro-β-carboline-3-carboxamide In the same manner as described in Example 53, (3S)-1,2,3,4-tetrahydro-β-carboline-3-carboxamide (0.71 g), triethylamine (0.46 ml), carbon disulfide (0.22 ml), 70% ethanol (20 ml) and 4-chlorobenzyl chloride (0.53 g) are reacted and treated to give the title compound (0.97 g, 71%) as white powder.

$[\alpha]_D^{20} +137.8°$ (c=1.0, ethyl acetate).

NMR (CDCl$_3$—DMSO—d$_6$, δ): 4.56 (s, 2H, N—CSSCH$_2$C$_6$H$_4$—p—Cl).

Mass (m/e): 415 (M+).

EXAMPLE 69

(3RS)-2-[(Methylthio)thiocarbonyl]-1,2,3,4-tetrahydro-β-carboline-3-(N,N-dimethyl)carboxamide In the same manner as described in Example 53, (3RS)-1,2,3,4-tetrahydro-β-carboline-3-(N,N-dimethyl)carboxamide (1.95 g), KOH (0.47 g), carbon disulfide (0.49 ml), 75% ethanol (30 ml) and methyl iodide (0.54 ml) are reacted and treated to give the title compound (0.78 g) as pale yellow powder.

NMR (CDCl$_3$—DMSO—d$_6$, δ): 2.69 (s, 3H, N—CSSCH$_3$), 3.23 (s, 3H, N—CH$_3$), 3.34 (s, 3H, N—CH$_3$).

Mass (m/e): 333 (M+).

EXAMPLE 70

(3S)-2-[(4-Chlorobenzylthio)thiocarbonyl]-1,2,3,4-tetrahydro-β-carboline-3-carboxylic acid benzylidenehydrazide (3S)-1,2,3,4-Tetrahydro-β-carboline-3-carboxylic acid hydrazide (2.44 g) is dissolved in dimethylsulfoxide (30 ml) and thereto is added benzaldehyde (2 ml). The mixture is stirred at room temperature for 2 hours and thereto are added triethylamine (1.49 ml) and carbon disulfide (0.64 ml). The mixture is stirred at room temperature for one hour and thereto is added dropwise 4-chlorobenzyl chloride (1.7 g). The mixture is stirred at room temperature for 3 hours and thereto is added water. The mixture is extracted with ethyl acetate. The extract is washed with water, dried and distilled to remove the solvent to give the title compound (3.26 g, 59%), as pale yellow powder.

Mass (m/e): 360 (M+—HSCH$_2$C$_6$H$_4$—p—Cl).

EXAMPLE 71

Methyl (3RS)-3-(N,N-Dimethylamino)methyl-1,2,3,4-tetrahydro-β-carboline-2-carbodithioate hydrochloride LiAlH$_4$ (0.4 g) is suspended in tetrahydrofuran (80 ml) and thereto is added dropwise a solution of (3RS)-1,2,3,4-tetrahydro-β-carboline-3-N,N-dimethylcarboxamide (1.22 g) in tetrahydrofuran (120 ml). The mixture is refluxed for 20 hours. After cooling, excess LiAlH$_4$ is decomposed with aqueous tetrahydrofuran. The reaction mixture is filtered and the residue is washed with tetrahydrofuran. The filtrate and washing liquid are combined, dried and distilled to remove the solvent to give crude (3RS)-3-(N,N-dimethylamino)methyl-1,2,3,4-tetrahydro-β-carboline (0.95 g). The crude product thus obtained is dissolved in 70% ethanol (15 ml) and thereto are added triethylamine (0.56 ml) and carbon disulfide (0.27 ml). The mixture is stirred for 30 minutes and thereto is added dropwise methyl iodide (0.27 ml). The mixture is stirred at room temperature for 3 hours. The mixture is distilled to remove the solvent. The residue is dissolved in ethyl acetate. The mixture is washed with water, dried and distilled to remove the solvent. The residue is purified by silica gel column chromatography (solvent, ethyl acetate:n-hexane=4:1) to give a free base of the title compound. The free base is treated with 10% HCl-ether to give the title compound (0.4 g) as powder.

NMR (CDCl$_3$—DMSO—d$_6$, δ): 2.52 (s, 3H, N—CSSCH$_3$), 2.81 (b.s, 6H, N(CH$_3$)$_2$).

Mass (m/e): 319 (M+).

EXAMPLE 72

Methyl (3RS)-3-(1H-tetrazol-5-yl)-1,2,3,4-tetrahydro-β-carboline-2-carbodithioate In the same manner as described in Example 53, (3RS)-3-(1H-tetrazol-5-yl)-1,2,3,4-tetrahydro-β-carboline (0.257 g), triethylamine (0.23 ml), carbon disulfide (0.05 ml), 70% ethanol (4 ml) and methyl iodide (0.055 ml) are reacted and treated. The product is crystallized from chloroform to give the title compound (75 mg), m.p. 203°–205° C. (decomp.).

Mass (m/e): 330 (M+).

EXAMPLE 73

(1RS,3RS)-cis-1-n-Propyl-2-[(methylthio)thiocarbonyl]-1,2,3,4-tetrahydro-β-carboline-3-carboxylic acid (1RS,3RS)-cis-n-Propyl-1,2,3,4-tetrahydro-β-carboline-3-carboxylic acid (450 mg) is dissolved in 80% methanol (10 ml), and thereto are added triethylamine (350 mg) and carbon disulfide (270 ml). The mixture is stirred at room temperature for 30 minutes, and methyl iodide (490 mg) is added to the mixture. The mixture is stirred at room temperature for 2 hours, and then distilled to remove the solvent. Water is added to the mixture, and the aqueous solution is acidified with 5% HCl, and extracted with ethyl acetate. The extract is washed with water, dried and then distilled to remove the solvent. The residue is treated with aqueous ethanol to give the title compound (350 mg, 59%) as pale yellow powder.

NMR (CDCl$_3$, δ): 2.72 (s, 3H, CSSCH$_3$).

Mass (m/e): 348 (M+), 300 (M+—CH$_3$SH).

EXAMPLE 74

(1RS,3SR)-trans-1-n-Propyl-2-[(methylthio)thiocarbonyl]-1,2,3,4-tetrahydro-β-carboline-3-carboxylic acid In the same manner as described in Example 73, (1RS,3SR)-trans-1-n-propyl-1,2,3,4-tetrahydro-β-carboline-3-carboxylic acid (0.9 g), triethylamine (0.4 g), carbon disulfide (0.3 g), methyl iodide (0.56 g) and 80% methanol (14 ml) are reacted and treated. The product is treated with aqueous ethanol to give the title compound (0.47 g) as pale yellow powder.

NMR (CDCl$_3$, δ): 2.60 (s, 3H, CSSCH$_3$).

Mass (m/e): 348 (M+), 300 (M+—CH$_3$SH).

REFERENCE EXAMPLE 1

(1) Methyl (1RS,3SR)-trans-2-benzyl-1-methyl-1,2,3,4-tetrahydro-β-carboline-3-carboxylate and methyl (1RS,3RS)-cis-2-benzyl-1-methyl-1,2,3,4-tetrahydro-β-carboline-3-carboxylate DL-N$^b$-Benzyltryptophan methyl ester (34.48 g) is dissolved in methanol (340 ml) and thereto is added acetaldehyde (5.23 g), and the mixture is heated at 50° C. for 5 hours. To the mixture is further added acetaldehyde (10.5 g), and the mixture is heated at 50° C. overnight and then distilled to remove the solvent. To the residue is added water, and the mixture is made alkaline with conc. NH$_4$OH and extracted with ethyl acetate. The extract is washed with water, dried and distilled to remove the solvent. The residue is purified by silica gel column chromatography (solvent: chloroform) to give methyl (1RS,3SR)-trans-2-benzyl-1-methyl-1,2,3,4-tetrahydro-β-carboline-3-carboxylate, which is recrystallized from methanol, yield: 16.1 g, colorless needles, m.p. 143°–144° C.; and further methyl (1RS,3RS)-cis-2-benzyl-1-methyl-1,2,3,4-tetrahydro-β-carboline-3-carboxylate, 3.15 g, as powder.

(2) Methyl (1RS,3SR)-trans-1-methyl-1,2,3,4-tetrahydro-β-carboline-3-carboxylate Methyl (1RS,3SR)-trans-2-benzyl-1-methyl-1,2,3,4-tetrahydro-β-carboline-3-carboxylate (14.0 g) is dissolved in methanol (600 ml), and thereto is added 10% Pd-C (1.0 g). The mixture is subjected to catalytic reduction under atmospheric pressure. After the reaction, the catalyst is removed by filtration and washed with methanol. The filtrate and the washing liquid are combined and distilled to remove the solvent. The residue is recrystallized from methanol-isopropyl ether to give the title compound (10.08 g, 98.5%) as colorless prisms, m.p. 152°–154° C.

(3) (1RS,3SR)-trans-1-Methyl-1,2,3,4-tetrahydro-β-carboline-3-carboxylic acid

Methyl (1RS,3SR)-trans-1-methyl-1,2,3,4-tetrahydro-β-carboline-3-carboxylate (2.44 g) is dissolved in methanol (30 ml), and thereto is added 1N NaOH (13 ml). The mixture is stirred at room temperature for 3 hours, and the solvent is distilled off under reduced pressure. The residue is dissolved in water and is acidified with 10% HCl. The precipitated crystals are collected by filtration, washed with water and dried to give the title compound (2.21 g, 90%) as colorless needles, m.p. 242°–244° C. (recrystallized from aqueous ethanol).

REFERENCE EXAMPLE 2

(1) (1RS,3RS)-cis-1-Ethyl-1,2,3,4-tetrahydro-β-carboline-3-carboxylic acid

Methyl (1RS,3RS)-cis-1-ethyl-1,2,3,4-tetrahydro-β-carboline-3-carboxylate (5.0 g) is dissolved in methanol (30 ml) and thereto is added 1N NaOH (30 ml). The mixture is stirred at room temperature for 1.5 hour, and the solvent is distilled off. The residue is dissolved in water and is acidified with 5% HCl. The precipitated crystals are collected by filtration, washed with water and dried to give the title compound (3.40 g, 72%) as colorless needles, m.p. 236°–237° C. (recrystallized from aqueous ethanol).

(2) (1RS,3SR)-trans-1-Ethyl-1,2,3,4-tetrahydro-β-carboline-3-carboxylic acid

In the same manner as described above (1) using methyl (1RS,3SR)-trans-1-ethyl-1,2,3,4-tetrahydro-β-carboline-3-carboxylate (2.58 g), 1N NaOH (15 ml) and methanol (30 ml), there is obtained the title compound (1.50 g, 61.4%) as colorless needles, m.p. 242°–243° C. (recrystallized from aqueous methanol).

REFERENCE EXAMPLE 3

(1) Methyl (1RS,3RS)-cis-1-butyl-1,2,3,4-tetrahydro-β-carboline-3-carboxylate and methyl (1RS,3SR)-trans-1-butyl-1,2,3,4-tetrahydro-β-carboline-3-carboxylate A mixture of DL-tryptophan methyl ester hydrochloride (30.49 g), n-valeraldehyde (12.4 g) and methanol (400 ml) is refluxed for 48 hours and then concentrated to about 1/5 volume. After cooling, the precipitates are separated by filtration and recrystallized from methanol to give methyl (1RS,3RS)-cis-1-butyl-1,2,3,4-tetrahydro-β-carboline-3-carboxylate hydrochloride (20.5 g, 53%), m.p. 218° C. (decomp.) The hydrochloride thus obtained is treated with aqueous ammonia and recrystallized from diisopropyl ether-isopropanol to give the corresponding free base, m.p. 85°–87° C.

The filtrate obtained after filtration of the precipitates is concentrated, and to the residue is added water. The aqueous solution is made alkaline with aqueous ammonia and then extracted with chloroform. The extract is washed with water, dried and distilled to remove the solvent. The residue is purified by silica gel column chromatography (solvent: chloroform-methanol=500:1) and then recrystallized from isopropyl ether-n-hexane to give methyl (1RS,3SR)-trans-1-butyl-1,2,3,4-tetrahydro-β-carboline-3-carboxylate (8.6 g), m.p. 102°–103° C.

(2) (1RS,3RS)-cis-1-Butyl-1,2,3,4-tetrahydro-β-carboline-3-carboxylic acid

In the same manner as described in Reference Example 2-(1) using methyl (1RS,3RS)-cis-1-butyl-1,2,3,4-tetrahydro-β-carboline-3-carboxylate (1.43 g), 1N NaOH (5.5 ml) and methanol (30 ml), there is obtained the title compound (1.06 g, 78%) as colorless needles, m.p. 215°–216° C. (recrystallized from methanol).

(3) (1RS,3SR)-trans-1-Butyl-1,2,3,4-tetrahydro-β-carboline-3-carboxylic acid

In the same manner as described in Reference Example 2-(1) using methyl (1RS,3SR)-trans-1-butyl-1,2,3,4-tetrahydro-β-carboline-3-carboxylate (2.0 g), 1N NaOH (8.2 ml) and methanol (35 ml), there is obtained the title compound (1.51 g, 79%) as colorless needles, m.p. 204°–205° C.

REFERENCE EXAMPLE 4

(1) (1RS,3RS)-cis-1-Hydroxymethyl-1,2,3,4-tetrahydro-β-carboline-3-carboxylic acid In the same manner as described in Reference Example 2-(1) using methyl (1RS,3RS)-cis-1-hydroxymethyl-1,2,3,4-tetrahydro-β-carboline-3-carboxylate (3.124 g), 1N NaOH (13.2 ml) and methanol (550 ml), there is obtained the title compound (2.66 g, 90%), m.p. 241°–242° C.

(2) (1RS,3SR)-trans-1-Hydroxymethyl-1,2,3,4-tetrahydro-β-carboline-3-carboxylic acid In the same manner as described in Reference Example 2-(1) using methyl (1RS,3SR)-trans-1-hydroxymethyl-1,2,3,4-tetrahydro-β-carboline-3-carboxylate (2.60 g), 10N NaOH (1.2 ml) and methanol (50 ml), there is obtained the title compound (1.60 g, 65%), m.p. 231°–233°C.

REFERENCE EXAMPLE 5

(3R)-9-Benzyl-1,2,3,4-tetrahydro-β-carboline-3-carboxylic acid

A mixture of D-N$^a$-benzyltryptophan (5.88 g) which is prepared in the same manner as described in Chem.

Pharm. Bull., 13, 88 (1956), 35% formalin (2 ml), 1N HCl (20 ml), ethanol (200 ml) and water (80 ml) is stirred overnight, and the reaction mixture is distilled to remove the solvent. The residue is recrystallized from ethanol to give the title compound (4.52 g, 73.8%) as colorless needles, m.p. 252°–253° C.

$[\alpha]_D^{20} +75.0°$ (c=1.0, 0.1N NaOH).

REFERENCE EXAMPLE 6

(1) Methyl (3S)-1,2,3,4-tetrahydro-β-carboline-3-carboxylate hydrochloride

L-Tryptophan methyl ester hydrochloride (5.09 g) is dissolved in methanol (60 ml) and thereto is added 35% formalin (1.89 g). The mixture is stirred at room temperature overnight, and the solvent is distilled off. The residue is recrystallized from methanol to give the title compound (4.42 g, 82.9%) as colorless needles, m.p. 250°–253° C.

$[\alpha]_D^{20} -67.2°$ (c=1.0, methanol).

(2) Methyl (3RS)-1,2,3,4-tetrahydro-β-carboline-3-carboxylate

In the same manner as described above (1) using DL-tryptophan methyl ester hydrochloride, there is obtained the title compound (75%) as colorless needles, m.p. 185°–187° C.

REFERENCE EXAMPLE 7

(1) Ethyl (3S)-1,2,3,4-tetrahydro-β-carboline-3-carboxylate (3S)-1,2,3,4-Tetrahydro-β-carboline-3-carboxylic acid (32.5 g) is suspended in ethanol (500 ml) and thereto is added dropwise $SOCl_2$ (13.0 ml) at 0° C. The mixture is refluxed for 8 hours and then distilled to remove the solvent. The residue is dissolved in water and is made alkaline with $NH_4OH$ and extracted with ethyl acetate. The extract is dried and distilled to remove the solvent. The residue is recrystallized from ethyl acetate-isopropyl ether to give the title compound (24.86 g, 68%) as colorless needles, m.p. 135°–137° C.

$[\alpha]_D^{20} -71.2°$ (c=1.0, EtOH).

(2) Ethyl (3R)-1,2,3,4-tetrahydro-β-carboline-3-carboxylate

In the same manner as described above (1) using (3R)-1,2,3,4-tetrahydro-β-carboline-3-carboxylic acid, there is obtained the title compound (54%) as colorless needles, m.p. 126°–128° C.

$[\alpha]_D^{20} +69.5°$ (c=1.0, methanol).

REFERENCE EXAMPLE 8

Methyl (3RS)-9-methyl-1,2,3,4-tetrahydro-β-carboline-3-carboxylate hydrochloride In the same manner as described in Reference Example 5 using DL-N$^a$-methyltryptophan methy ester hydrochloride (6.50 g), 35% formalin (2.8 ml) and methanol (150 ml), there is obtained the title compound (6.21 g, 91.4%) as colorless needles, m.p. 259°–262° C. (decomp.) (recrystallized from methanol).

REFERENCE EXAMPLE 9

(1) (3RS)-2-Benzyloxycarbonyl-1,2,3,4-tetrahydro-β-carboline-3-carboxamide (3RS)-2-Benzyloxycarbonyl-1,2,3,4-tetrahydro-β-carboline-3-carboxylic acid (21 g) which is prepared in the same manner as disclosed in Chem. Pharm. Bull., 25, 1559 (1977) is dissolved in tetrahydrofuran (320 ml), and thereto is added triethylamine (8.4 ml) and is further added dropwise ethyl chlorocarbonate (6.6 g). The mixture is stirred at −10° C. for 40 minutes. To the mixture is added dropwise conc. aqueous ammonia (5.9 ml) at one time. The mixture is stirred at 0° C. for 3 hours. The reaction mixture is filtered to remove triethylamine hydrochloride. The filtrate is distilled under reduced pressure, and the residue is extracted with ethyl acetate. The ethyl acetate layer is washed well with saturated aqueous sodium bicarbonate solution and water and then dried. The solution is distilled under reduced pressure to remove ethyl acetate and the residue is crystallized from n-hexane to give the title compound (17.9 g, 85%), m.p. 206°–207° C. (decomp.).

(2) (3RS)-1,2,3,4-Tetrahydro-β-carboline-3-carboxamide (3RS)-2-Benzyloxycarbonyl-1,2,3,4-tetrahydro-β-carboline-3-carboxamide (2.47 g) is dissolved in ethanol (350 ml) and thereto are added acetic acid (0.02 ml) and 10% Pd-C (1.0 g). The mixture is subjected to catalytic reduction under atmospheric pressure. After the reaction, the catalyst is removed by filtration and washed with ethanol. The filtrate and the washing liquid are combined and distilled to remove the solvent. The residue is crystallized from ether to give the title compound (1.21 g, 79%), m.p. 212°–216° C.

In the same manner as described above (1) and (2) using (3S)-2-benzyloxycarbonyl-1,2,3,4-tetrahydro-β-carboline-3-carboxylic acid, there is obtained (3S)-1,2,3,4-tetrahydro-β-carboline-3-carboxamide as powder.

REFERENCE EXAMPLE 10

(1) (3RS)-2-Benzyloxycarbonyl-1,2,3,4-tetrahydro-β-carboline-3-N,N-dimethylcarboxamide (3RS)-2-Benzyloxycarbonyl-1,2,3,4-tetrahydro-β-carboline-3-carboxylic acid (21 g) is dissolved in tetrahydrofuran (200 ml) and thereto are added 1-hydroxybenzotriazole (8.1 g), dimethylamine hydrochloride (4.9 g), triethylamine (8.4 ml) and DCC (i.e. N,N'-dicyclohexylcarbodiimide) (12.4 g), and the mixture is stirred at 5° C. for one hour and further at room temperature for 16 hours. The reaction mixture is distilled under reduced pressure to remove tetrahydrofuran, and to the residue is added ethyl acetate (500 ml). After removing the precipitated dicyclohexylurea by filtration, the filtrate is washed with 10% HCl, water, saturated aqueous sodium bicarbonate solution and water in this order, dried and then distilled under reduced pressure to remove ethyl acetate. The resulting crystals are recrystallized from ethyl acetate to give the title compound (15.06 g, 67%), m.p. 179°–180° C.

(2)
(3RS)-1,2,3,4-Tetrahydro-β-carboline-3-N.N-dimethylcarboxamide (3RS)-2-Benzyloxycarbonyl-1,2,3,4-tetrahydro-β-carboline-3-N,N-dimethylcarboxamide (3.77 g) is dissolved in a mixture of ethanol (200 ml)—acetic acid (20 ml)—water (20 ml), and thereto is added 10% Pd-C (4 g). The mixture is subjected to catalytic reduction. After the reaction, the catalyst is removed by filtration, and the filtrate is concentrated. The residue is crystallized from ether to give the title compound (2.2 g, 91%), m.p. 199°–200° C. (decomp.).

REFERENCE EXAMPLE 11
(3S)-1,2,3,4-Tetrahydro-β-carboline-3-carboxylic acid hydrazide A mixture of ethyl (3S)-1,2,3,4-tetrahydro-β-carboline-3-carboxylate (4.9 g), hydrazine hydrate (10 ml) and dimethylformamide (50 ml) is allowed to stand at room temperature overnight. The reaction mixture is is distilled under reduced pressure to remove the solvent. The residue is treated with ethyl acetate to give the title compound (3.40 g, 74%) as powder.

IR $\nu_{max}^{Nujol}$ (cm$^{-1}$): 1670.

REFERENCE EXAMPLE 12
(1) (3RS)-2-Benzyloxycarbonyl-3-cyano-1,2,3,4-tetrahydro-β-carboline (3RS)-2-Benzyloxycarbonyl-1,2,3,4-tetrahydro-β-carboline-3-carboxamide (1.05 g) is dissolved in pyridine (6 ml) and thereto is added dropwise POCl$_3$ (0.37 ml) at −5° C. The mixture is stirred at the same temperature for 2 hours, and the reaction mixture is poured onto ice-water and extracted with ethyl acetate. The ethyl acetate layer is washed with 10% HCl and water and dried, and then the solvent is distilled off to give the title compound (0.81 g, 82%) as white powder.

IR $\nu_{max}^{nujol}$ (cm$^{-1}$): 2210 (CN).
Mass (m/e): 331 (M+).

(2) (3RS)-2-Benzyloxycarbonyl-3-(1H-tetrazol-5-yl)-1,2,3,4-tetrahydro-β-carboline A mixture of (3RS)-2-Benzyloxycarbonyl-3-cyano-1,2,3,4-tetrahydro-β-carboline (0.663 g), NaN$_3$ (0.143 g), NH$_4$Cl (0.118 g) and dimethylformamide (2 ml) is stirred at 95°–100° C. for 6 hours. The reaction mixture is cooled and then poured onto ice-water, adjusted to pH 2 with 10% HCl and extracted with ethyl acetate. The ethyl acetate layer is washed with water, dried and distilled to remove the solvent. The residue is crystallized from ethyl acetate to give the title compound (0.358 g), m.p. 218°–219° C. (decomp.).

(3) (3RS)-3-(1H-Tetrazol-5-yl)-1,2,3,4-tetrahydro-β-carboline (3RS)-2-Benzyloxycarbonyl-3-(1H-tetrazol-5-yl)-1,2,3,4-tetrahydro-β-carboline (0.3 g) is dissolved in acetic acid (1 ml) and thereto is added dropwise a 25% solution of HBr in acetic acid (2 ml). The mixture is stirred at room temperature for 20 minutes, and thereto is added ether. The precipitates are collected by filtration, washed with ether and dried to give the title compound (0.257 g, quantitatively) as pale yellow powder.

REFERENCE EXAMPLE 13
(1) Methyl (1RS,3RS)-cis-1-n-propyl-1,2,3,4-tetrahydro-β-carboline-3-carboxylate and methyl (1RS,3SR)-trans-1-n-propyl-1,2,3,4-tetrahydro-β-carboline-3-carboxylate A mixture of DL-tryptophan methyl ester hydrochloride (33 g), n-butylaldehyde (21.04 g) and methanol (450 ml) is refluxed for 48 hours and then concentrated. After cooling, the precipitates are collected by filtration, and recrystallized from methanol to give methyl (1RS,3RS)-cis-1-n-propyl-1,2,3,4-tetrahydro-β-carboline-3-carboxylate hydrochloride (15.4 g) as colorless prisms, m.p. 205°–207° C.

The filtrate obtained above is concentrated, and water is added to the residue. The aqueous solution is made alkaline with aqueous ammonia, and extracted with chloroform. The extract is washed with water, dried and then distilled to remove the solvent. The residue is purified by silica gel column chromatography (solvent: chloroform-methanol=300:1), whereby the following compounds are obtained.

Methyl (1RS,3RS)-cis-1-n-propyl-1,2,3,4-tetrahydro-β-carboline-3-carboxylate:
Colorless needles
M.p. 98°–100° C. (recrystallized from diisopropyl ether-isopropanol)

Methyl (1RS,3SR)-trans-1-n-propyl-1,2,3,4-tetrahydro-β-carboline-3-carboxylate:
Colorless prisms
M.p. 116°–118° C. (recrystallized from diisopropyl ether)

(2) (1RS,3RS)-cis-1-n-Propyl-1,2,3,4-tetrahydro-β-carboline-3-carboxylic acid A mixture of methyl (1RS,3RS)-cis-1-n-propyl-1,2,3,4-tetrahydro-β-carboline-3-carboxylate (1.3 g), 1N NaOH (5.5 ml) and methanol (8 ml) is stirred at room temperature for 1.5 hours. The mixture is distilled under reduced pressure to remove methanol. The residue is adjusted to pH 4 with 10% HCl, and the precipitated crystals are collected by filtration, washed with water and then dried to give the title compound (1.0 g, 81%) as colorless needles, m.p. 225°–226° C.

IR $\nu_{max}^{nujol}$ (cm$^{-1}$): 1640.

(3) (1RS,3SR)-trans-1-n-Propyl-1,2,3,4-tetrahydro-β-carboline-3-carboxylic acid In the same manner as described above (2) using methyl (1RS,3SR)-trans-1-n-propyl-1,2,3,4-tetrahydro-β-carboline-3-carboxylate (1.36 g), 1N NaOH (6 ml) and methanol (20 ml), there is obtained the title compound (1.01 g, 78%) as colorless needles, m.p. 210°–211° C.

IR $\nu_{max}^{nujol}$ (cm$^{-1}$): 1635.

What is claimed is:

1. A tetrahydro-β-carboline derivative of the formula:

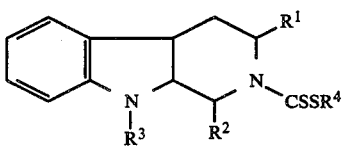

wherein

R$^1$ is carboxyl, a lower alkoxycarbonyl, carbamoyl, an N,N-di-lower alkylcarbamoyl, an N-(phenyl-substituted lower alkylidenamino)carbamoyl, an [N,N-di(lower alkyl)-amino]-lower alkyl, or a tetrazolyl;

R$^2$ is a hydrogen atom, a lower alkyl, or a hydroxy-lower alkyl group, or

R$^2$ is combined with R$^1$ to form a group —CO—O—CH$_2$—;

R$^3$ is a hydrogen atom, a lower alkyl, a phenyl-lower alkyl, or a group of the formula: —CCS—R$^4$;

R$^4$ is a hydrogen atom, a C1–C10 alkyl group, or a group of the formula: —(CH$_2$)$_n$Y$^1$;

n is 0, 1 or 2,

Y$^1$ is a lower alkenyl, a phenyl-substituted lower alkenyl, an N,N-di(lower alkyl)amino, a lower alkylmercapto, a lower alkoxycarbonyl, benzoyl, naphthyl, a cycloalkyl of 5 to 6 carbon atoms, thienyl, furyl, pyridyl, phenyl, or a phenyl having one or two substituents selected from the group consisting of a halogen, amino, benzloxycarbonylamino, formylamino, a lower alkoxy, nitro, a lower alkyl, carboxyl and a halogenated lower alkyl group, or a pharmaceutically acceptable salt thereof.

2. A pharmaceutically acceptable salt of the compound of claim 1, wherein R$^1$ is carboxyl, an N-(phenyl-substituted lower alkylidenamino)carbomoyl, an [N-N-di(lower alkyl)amino]-lower alkyl or a tetrazolyl.

3. The compound of claim 1, which is (3S), (3R) or (3RS)-2-[(methylthio)thiocarbonyl]-1,2,3,4-tetrahydro-β-carboline-3-carboxylic acid or a pharmaceutically acceptable salt thereof.

4. The compound of claim 1, which is (1S,3S)-cis-1-methyl-2-[(methylthio)thiocarbonyl]-1,2,3,4-tetrahydro-β-carboline-3-carboxylic acid or a pharmaceutically acceptable salt thereof.

5. The compound of claim 1, which is (1RS,3RS)-cis-1-hydroxymethyl-2-[(methylthio)thiocarbonyl]-1,2,3,4-tetrahydro-β-carboline-3-carboxylic acid or a pharmaceutically acceptable salt thereof.

6. The compound of claim 1, in which

R$^1$ is carboxyl, methoxycarbonyl, ethoxycarbonyl, isopropoxycarbonyl, carbamoyl, N,N-dimethylcarbamoyl, N-(benzylidenamino)carbamoyl, (N,N-dimethylamino)methyl, or tetrazolyl, R$^2$ is a hydrogen atom, methyl, ethyl, n-propyl, n-butyl or hydroxymethyl, or R$^2$ is combined with R$^1$ to form a group: —CO—O—CH$_2$—, R$^3$ is a hydrogen atom, methyl, benzyl, or a group of the formula: —CSS—R$^4$, R$^4$ is a hydrogen atom, methyl, ethyl, n-propyl, n-butyl, n-decyl or a group of the formula: —(CH$_2$)$_n$Y$^1$, n is 0, 1 or 2, and Y$^1$ is vinyl, styryl, N,N-dimethylamino, methylmercapto, ethoxycarbonyl, benzoyl, naphthyl, cyclohexyl, 2-thienyl, 2-furyl, 2-pyridyl, phenyl, or a phenyl having one or two substituents selected from the group consisting of chlorine, amino, benzyloxycarbonylamino, formylamino, methoxy, nitro, methyl, carboxyl and trifluoromethyl.

7. A pharmaceutically acceptable salt of the compound of claim 6, wherein R$^1$ is carboxyl, N-(benzylidenamino)carbamoyl, (N,N-dimethylamino)methyl or tetrazolyl.

8. The compound of claim 6, in which

R$^1$ is carboxyl, methoxycarbonyl, ethoxycarbonyl, carbamoyl, N,N-dimethylcarbamoyl, (N,N-dimethylamino)methyl or tetrazolyl, R$^2$ is a hydrogen atom, methyl, ethyl, n-propyl or hydroxymethyl, R$^3$ is a hydrogen atom, methyl, benzyl, or a group of the formula: —CSSR—R$^4$, R$^4$ is a hydrogen atom, methyl, ethyl, n-propyl, allyl, cinnamyl, 2-thenyl, benzyl, 4-chlorobenzyl, 4-aminobenzyl, 4-(benzyloxycarbonylamino)benzyl, 4-(formylamino)benzyl, 4-methoxybenzyl or 4-methylbenzyl.

9. A pharmaceutically acceptable salt of the compound of claim 8, wherein R$^1$ is carboxyl, (N,N-dimethylamino)methyl or tetrazolyl.

10. The compound of claim 8, in which

R$^1$ is carboxyl, methoxycarbonyl, N,N-dimethylcarbamoyl, (N,N-dimethylamino)methyl or tetrazolyl, R$^2$ is a hydrogen atom, methyl, ethyl, n-propyl or hydroxymethyl, R$^3$ is a hydrogen atom or a group of the formula:

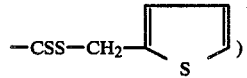

R$^4$ is a hydrogen atom, methyl, ethyl, 2-thenyl or 4-aminobenzyl.

11. A pharmaceutically acceptable salt of the compound of claim 10, wherein R$^1$ is carboxyl, (N,N-dimethylamino)methyl or tetrazolyl.

12. A composition for treating or preventing liver damage, wherein the liver damage is a liver disease associated with centrilobular necrosis, periportal necrosis, discrete lobular necrosis and/or mesenchymal reaction, fatty liver, drug-induced hepatopathy, viral hepatitis, alcoholic hepatitis, jaundice or hepatocirrhosis, which comprises as the essential active ingredient a therapeutically or prophylactically effective amount of a tetrahydro-β-carboline derivative as claimed in claim 1 in admixture with a pharmaceutically acceptable carrier or diluent.

13. A composition for treating or preventing liver damage, wherein the liver damage is a liver disease associated with centrilobular necrosis, periportal necrosis, discrete lobular necrosis and/or mesenchymal reaction, fatty liver, drug-induced hepatopathy, viral hepatitis, alcoholic hepatitis, jaundice or hepatocirrhosis, which comprises as the essential active ingredient a therapeutically or prophylactically effective amount of a tetrahydro-β-carboline derivative as claimed in claim 2 in admixture with a pharmaceutically acceptable carrier or diluent.

14. A composition for treating or preventing liver damage, wherein the liver damage is a liver disease associated with centrilobular necrosis, periportal necrosis, discrete lobular necrosis or mesenchymal reaction, fatty liver, drug-induced hepatopathy, viral hepatitis, alcoholic hepatitis, jaundice or hepatocirrhosis, which comprises as the essential active ingredient a therapeutically or prophylactically effective amount of a tetrahydro-β-carboline derivative as claimed in claim 6 in admixture with a pharmaceutically acceptable carrier or diluent.

15. A method for treating or preventing liver damage, wherein the liver damage is a liver disease associated with centrilobular necrosis, periportal necrosis, discrete lobular necrosis or mesenchymal reaction, fatty liver, drug-induced hepatopathy, viral hepatitis, alcoholic hepatitis, jaundice or hepatocirrhosis, which comprises orally or parenterally administering to a patient affected with said liver damage a therapeutically or prophylactically effective amount of a tetrahydro-β-carboline derivative as claimed in claim 1.

16. A method for treating or preventing liver damage, wherein the liver damage is a liver disease associated with centrilobular necrosis, periportal necrosis, discrete lobular necrosis or mesenchymal reaction, fatty liver, drug-induced hepatopathy, viral hepatitis, alcoholic hepatitis, jaundice or hepatocirrhosis, which comprises orally or parenterally administering to a patient affected with said liver damage a therapeutically or prophylactically effective amount of a tetrahydro-β-carboline derivative as claimed in claim 2.

17. A method for treating or preventing liver damage, wherein the liver damage is a liver disease associated with centrilobular necrosis, periportal necrosis, discrete lobular necrosis or mesenchymal reaction, fatty liver, drug-induced hepatopathy, viral hepatitis, alcoholic hepatitis, jaundice or hepatocirrhosis, which comprises orally or parenterally administering to a patient affected with said liver damage a therapeutically or prophylactically effective amount of a tetrahydro-β-carboline derivative as claimed in claim 6.

18. A method for treating or preventing liver damage, wherein the liver damage is a liver disease associated with centrilobular necrosis, periportal necrosis, discrete lobular necrosis or mesenchymal reaction, fatty liver, drug-induced hepatopathy, viral hepatitis, alcoholic hepatitis, jaundice or hepatocirrhosis, which comprises orally or parenterally administering to a patient affected with said liver damage the composition claimed in claim 12.

19. A method for treating or preventing liver damage, wherein the liver damage is a liver disease associated with centrilobular necrosis, periportal necrosis, discrete lobular necrosis or mesenchymal reaction, fatty liver, drug-induced hepatopathy, viral hepatitis, alcoholic hepatitis, jaundice or hepatocirrhosis, which comprises orally or parenterally administering to a patient affected with said liver damage the composition claimed in claim 14.

20. A method for treating or preventing liver damage, wherein the liver damage is a liver disease associated with centrilobular necrosis, periportal necrosis, discrete lobular necrosis or mesenchymal reaction, fatty liver, drug-induced hepatopathy, viral hepatitis, alcoholic hepatitis, jaundice or hepatocirrhosis, which comprises orally or parenterally administering to a patient affected with said liver damage the composition claimed in claim 13.

21. A pharmaceutically acceptable salt of the compound of claim 1, wherein $R^4$ is a hydrogen atom or a group of the formula: —$(CH_2)_nY^1$, n is 0, 1 or 2 and $Y^1$ is an N,N-di(lower alkyl)amino, pyridyl or a phenyl substituted by carboxyl or amino.

22. A pharmaceutically acceptable salt of the compound of claim 6, wherein $R^4$ is a hydrogen atom or a group of the formula: —$(CH_2)_nY^1$, n is 0, 1 or 2 and $Y^1$ is an N,N-dimethylamino, pyridyl or a phenyl substituted by carboxyl or amino.

23. A pharmaceutically acceptable salt of the compound of claim 8, wherein $R^4$ is a hydrogen atom or 4-aminobenzyl.

24. A pharmaceutically acceptable salt of the compound of claim 10, wherein $R^4$ is a hydrogen atom or 4-aminobenzyl.

25. A composition for treating or preventing liver damage, wherein the liver damage is a liver disease associated with centrilobular necrosis, periportal necrosis, discrete lobular necrosis or mesenchymal reaction, fatty liver, drug-induced hepatopathy, viral hepatitis, alcoholic hepatitis, jaundice or hepatocirrhosis, which comprises as the essential active ingredient a therapeutically or prophylactically effective amount of a tetrahydro-β-carboline derivative as claimed in claim 21 in admixture with a pharmaceutically acceptable carrier or diluent.

26. A method for treating or preventing liver damage, wherein the liver damage is a liver disease associated with centrilobular necrosis, periportal necrosis, discrete lobular necrosis or mesenchymal reaction, fatty liver, drug-induced hepatopathy, viral hepatitis, alcoholic hepatitis, jaundice or hepatocirrhosis, which comprises orally or parenterally administering to a patient affected with said liver damage a therapeutically or prophylactically effective amount of a tetrahydro-β-carboline derivative as claimed in claim 21.

27. A method for treating or preventing liver damage, wherein the liver damage is a liver disease associated with centrilobular necrosis, periportal necrosis, discrete lobular necrosis or mesenchymal reaction, fatty liver, drug-induced hepatopathy, viral hepatitis, alcoholic hepatitis, jaundice or hepatocirrhosis, which comprises orally or parenterally administering to a patient affected with said liver damage a therapeutically or prophylactically effective amount of the composition as claimed in claim 25.

* * * * *